United States Patent
Admyre et al.

(10) Patent No.: US 10,046,006 B2
(45) Date of Patent: *Aug. 14, 2018

(54) COMPOUNDS AND METHODS FOR REDUCING THE RECRUITMENT AND/OR MIGRATION OF POLYMORPHONUCLEAR CELLS

(71) Applicant: InDex Pharmaceuticals AB, Stockholm (SE)

(72) Inventors: Charlotte Admyre, Vendelsö (SE); Lars-Göran Axelsson, Tierp (SE); Oliver Von Stein, Upplands Väsby (SE); Arezou Zargari, Solna (SE)

(73) Assignee: InDex Pharmaceuticals AB, Stockholm (SE)

( * ) Notice: Subject to any disclaimer, the term of this patent is extended or adjusted under 35 U.S.C. 154(b) by 0 days.

This patent is subject to a terminal disclaimer.

(21) Appl. No.: 14/512,036

(22) Filed: Oct. 10, 2014

(65) Prior Publication Data
US 2015/0099799 A1    Apr. 9, 2015

Related U.S. Application Data

(63) Continuation of application No. 13/127,217, filed as application No. PCT/SE2009/051227 on Oct. 28, 2009, now Pat. No. 8,877,724.

(60) Provisional application No. 61/111,284, filed on Nov. 4, 2008.

(30) Foreign Application Priority Data

Nov. 4, 2008   (SE) .................................. 0802338

(51) Int. Cl.
| A61K 48/00 | (2006.01) |
| A61K 31/7088 | (2006.01) |
| A61K 31/7125 | (2006.01) |
| C12N 15/113 | (2010.01) |
| C12N 15/117 | (2010.01) |
| A61K 45/06 | (2006.01) |

(52) U.S. Cl.
CPC ...... *A61K 31/7088* (2013.01); *A61K 31/7125* (2013.01); *A61K 45/06* (2013.01); *C12N 15/117* (2013.01); *C12N 15/1138* (2013.01); *C12N 2310/17* (2013.01)

(58) Field of Classification Search
CPC ....................................................... A61K 48/00
See application file for complete search history.

(56) References Cited

U.S. PATENT DOCUMENTS

| 6,172,208 B1 * | 1/2001 | Cook .......................... 536/23.1 |
| 6,489,311 B1 | 12/2002 | Kennedy |
| 8,309,529 B2 | 11/2012 | Karlsson et al. |
| 8,637,479 B2 | 1/2014 | Bandholtz et al. |
| 2007/0298021 A1 | 12/2007 | Von Stein et al. |
| 2011/0280934 A1 | 11/2011 | Karlsson et al. |

FOREIGN PATENT DOCUMENTS

| WO | 2005/080568 A1 | 9/2005 |
| WO | 2007/030580 A1 | 3/2007 |
| WO | 2008/136748 A1 | 11/2008 |

OTHER PUBLICATIONS

Agrawal eta., Antisense therapeutics: is it as simple as complementary base recognition? Mol Med Today. Feb. 2000;6(2):72-81.*
Brown et al., Gene delivery with synihetic (non viral) carriers. Int J Pharm. Oct. 23, 2001;229(1-2):1-21.*
Levente et al, The Journal of Immunology, 176:1196-1202 (2006).
Stevens et al, Journal of Cerebral Blood Flow & Metabolism, 28(5):1040-1047 (2008).
Nian et al., Circulation Research, 94:1543-1553 (2004).
Weathington et al, Nature Medicine, 12:317-323 (2006).
Lofberg, Journal of Gastrointestinal and Digestive System, 4(6):1-9 (2014).
Musch, Clinical: Therapy and Observation, "Low colectomy rate in treatment refractory ulcerative colitis patients following treatment with the Toll-like receptor 9 agonist DIMS0150", Abstract P441 (2013).

* cited by examiner

*Primary Examiner* — Maria G Leavitt
(74) *Attorney, Agent, or Firm* — Porter, Wright, Morris and Arthur LLP

(57) ABSTRACT

Methods for reducing recruitment, migration, or both recruitment and migration of polymorphonuclear cells to a site of inflammation in an organ of a human patient comprise administering locally to the organ or systemically to the patient in need thereof an isolated oligonucleotide selected from the group consisting of SEQ ID NO: 8 (IDX9059); SEQ ID NO: 14 (IDX9052); SEQ ID NO: 7 (IDX9054); SEQ ID NO: 6 (IDX9045); SEQ ID NO: 1 (IDX9005); SEQ ID NO: 9 (IDX9074); SEQ ID NO: 3 (IDX9022); SEQ ID NO: 2 (IDX9010); SEQ ID NO: 4 (IDX9030); and SEQ ID NO: 13 (IDX0150).

25 Claims, 23 Drawing Sheets

Figure 1A:
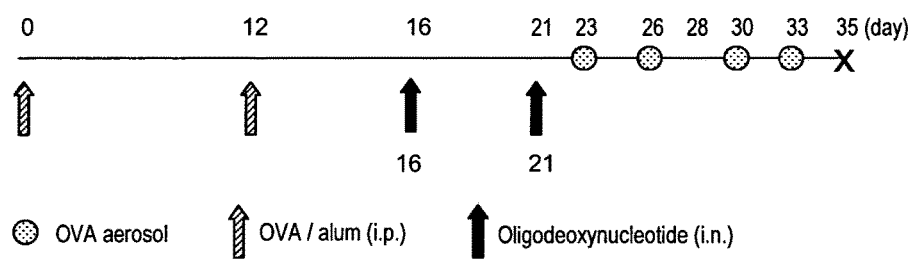

COMPOUNDS AND METHODS FOR REDUCING THE RECRUITMENT AND/OR MIGRATION OF POLYMORPHONUCLEAR CELLS

The Sequence Listing submitted herewith, entitled "Oct-10-2014-186891A_ST25.txt", created Oct. 10, 2014 and having a size of 3427 bytes, is incorporated herein by reference.

TECHNICAL FIELD

The present inventions concerns methods and compounds for reducing the recruitment and/or migration of polymorphonuclear cells, and in particular compounds and methods for the prevention, treatment or alleviation of various conditions where the properties and behaviour of polymorphonuclear cells play a role in the pathogenesis.

BACKGROUND

Inflammation is a general term for the mechanisms by which the body reacts to infection, irritation and other injury, mobilizing components of the immune system. Polymorphonuclear cells are recruited in the early stages of inflammation, and migrate to the site of inflammation. Chemokines and their receptors, together with other chemoattractants, are key mediators for PMN migration. Examples of chemoattractants are IL-8 and $LTB_4$, which by binding to their receptors CXCR1/CXCR2 and BLT1, respectively, play a crucial role in the recruitment of PMN to the site of inflammation. Importantly, inflammation plays a role in numerous conditions, not only diseases normally classified as inflammatory diseases.

Ischemia is an absolute or relative shortage of the blood supply to an organ that results in tissue damage because of a lack of oxygen and nutrients. The heart, the brain, and the kidneys are among the organs that are the most sensitive to inadequate blood supply. Different treatment strategies are used depend on the organs involved and the cause of ischemia. One example is, after an acute heart ischemia (myocardial infarction), either a thrombolytic therapy or primary percutaneous coronary intervention has to be used to restore blood flow (myocardial reperfusion) in the infarct-related coronary artery. However, the restoration of blood after an ischemic episode causes the death of cardiac myocytes that were viable immediately before myocardial reperfusion. This myocardial injury is termed lethal reperfusion injury which increases the final size of myocardial infarct. Myocardial ischemia and reperfusion injury are believed to be associated with inflammatory reactions involving various types of cells and cytokines (Entman and Smith 1994).

Another example is stroke, and in particular ischemic stroke. In an ischemic stroke, blood supply to one or more parts of the brain is decreased, leading to dysfunction and necrosis of the brain tissue in those parts. There are several underlying causes for an ischemic stroke: thrombosis (obstruction of a blood vessel by a blood clot forming locally), embolism (obstruction of a blood vessel due to an embolus formed elsewhere in the body), systemic hypoperfusion (general decrease in blood supply, e.g. as a consequence of shock) and venous thrombosis.

Embolism is a serious condition which can lead to limited blood supply to organs or tissues, downstream from the embolus. Embolism, mentioned above as one causative factor in stroke, is known to cause obstruction in other organs, frequently in the lungs, kidneys, or liver, but also in the lower limbs. An embolus can form spontaneously, for example when plack is dislocated from the walls of a blood vessel and travels in the blood stream. Emboli may also form as a result of trauma, for example fat emboli from complicated fractures or blood clots (thrombi) from the site of haemorrhage. Patients undergoing surgery are also at risk, as both thrombi and fat emboli may form during the surgical intervention. Also immobility, obesity and cancer are risk factors, known to be associated with embolism.

Mesenteric ischemia is a medical condition in which inflammation and injury of the small intestine result from inadequate blood supply. Causes of the reduced blood flow can include changes in the systemic circulation (e.g. low blood pressure) or local factors such as constriction of blood vessels or a blood clot. Other intestinal disorders and conditions potentially leading to ischemia include ileus, distention, invagination, and volvulus, where abnormal orientation of the intestines, disruption of the peristaltic movement, and other conditions can lead to reduced blood flow, inflammation, and eventually ischemia. For example ileus may increase adhesion formation, because intestinal segments are in prolonged contact, allowing fibrous adhesions to form, and intestinal distention can cause serosal injury and ischemia. Such disorders can arise as a result of surgical intervention, either during the surgery or during recovery, as a result of trauma, burns, shock or various etiology etc and may lead to multiple organ failure.

Polymorphonuclear cells (PMNs), in particular polymorphonuclear neutrophils, which constitute the majority of the blood leukocytes are drawn into the infarct zone by chemoattractants during the first 6 hours of myocardial reperfusion, and during the next 24 hours they migrate into the myocardial tissue. This process is facilitated by cell adhesion molecules. The neutrophils cause vascular plugging and release degradative enzymes and reactive oxygen species (Vinten-Johansen J, 2004). Therefore neutrophils are the primary target for the purpose of the treatment or prevention of inflammation. Several interventions were aimed at reducing neutrophils from the infarct area during myocardial reperfusion e.g. leukocyte-depleted blood, antibodies against the cell adhesion molecules, and pharmacologic inhibitors of complement activation. However, the corresponding clinical studies have not shown any meaningful cardioprotective effect of such interventions (Reviewed in Yelton, 2007).

PMN accumulation and activation has been shown to play a central role in the pathogenesis of a wide range of disease states as diverse as rheumatoid arthritis, atherosclerosis, ulcerative colitis, psoriasis, and ischemic damage. Hence the elucidation of endogenous regulatory mechanisms that can control neutrophil functions are of considerable therapeutic interest. Extensive efforts have been spent on identifying drug candidates, and one approach is represented by the use of peptide compounds, which bind to the αM integrin I-domain and inhibit its complex formation with proMMP-9, thereby preventing neutrophil migration (See e.g. WO2004/110477)

Another approach is the use of lipoxin and lipoxin derivatives, small lipophilic compounds which have been shown to inhibit leukocyte recruitment and PMN infiltration in animal models of inflammation (See e.g. WO2000/055109).

Yet another approach is the use of antibodies. In the early 1990-ties, a potent CD47-specific antibody (Ab), C5/D5, was identified that was capable of inhibiting PMN migration across vascular endothelium, collagen-coated filters and intestinal epithelium without inhibiting β2 integrin-mediated adhesion (Parkos, et al., 1996). At the same time, it was shown that anti-CD47 also inhibited PMN migration across endothelial monolayers (Cooper, et al., Proc Natl Acad Sci USA, 92: 3978, 1995). Subsequent studies with CD47 knockout mice have confirmed the importance of CD47 in PMN migration in vivo suggesting that CD47 plays a role in regulating the rate of PMN recruitment to sites of infection. (Lindberg et al., 1996).

Transplantation is another application where the consequences of reperfusion ischemia must be considered. Transplantation means the transfer of cells, tissue or parts of organs or entire organs from one location to another. Transplants can be autologous, so called autografts, where mainly cells are taken from an individual and given back to that same individual. More frequently, the term transplant is used for cells, tissue or organs taken from one person, the donor, and given to another person, the recipient. Kidney transplants are the most commonly performed. Transplants of the heart, liver and lungs are also regularly carried out. As medicine advances, other vital organs including the pancreas and small bowel are also being used in transplants. Tissue such as corneas, heart valves, skin and bone can also be donated.

For practical reasons, a transplant needs to be stored outside the body for a period of time, to allow for transport, functional testing, tissue typing and matching the donor and the recipient. Since the advent of transplantation, organs to be transplanted have been kept in cold ischemic storage. Although this method was intended to help reduce the extent of organ damage during transport, significant damage still occurs. The more time that passes, the more serious damage. Different technical and chemical solutions have been proposed. However, as the number of persons in need of a transplant far exceeds the number of donors, and as the procedure is very complicated, costly and stressful for all parties, there remains a need for improvements that increase the chance of a successful transplantation. Minimizing organ damage during storage and transport is an important issue.

WO 2005/080568 concerns the use of NF-kB inhibiting compounds for the prevention or reduction of the extent of secondary ischemic damage in a mammal. The NF-kB inhibiting compounds are chosen from the group consisting of: an antisense NF-KB p65 subunit oligonucleotide; a dominant-negative form of the NF-KB p65 subunit; a decoy; ribosome inhibitors; enzymatic RNA against NF-KB p65; and siRNA constructs.

WO 2007/030580 concerns methods of protecting cells against cytotoxic insult, involving the administration of a composition including an agent that binds to and activates a Toll-like receptor to a subject, optionally in combination with administering an ASIC inhibitor. The methods are stated to be applicable to the protection of neural and non-neural cells. For example, methods of protecting a neural cell against excitotoxic brain injury are provided. Methods for preparing medicaments for the prophylactic treatment of excitotoxic injury, ischemia and/or hypoxia are also provided.

WO 2007/030581 is a parallel application to the above WO 2007/030580, focussing on the administration of a CpG oligonucleotide for protecting cells against cytotoxic insult.

SUMMARY

The present inventors have surprisingly shown that specific oligonucleotide compounds influence the properties and behaviour of polymorphonuclear cells, in particular the recruitment and/or migration of polymorphonuclear cells to a site of inflammation, and that they through this mechanism have utility in the prevention, treatment and/or alleviation of various diseases.

The inventors make available oligonucleotides and methods of their use in therapy, as well as in the manufacture of pharmaceutical compositions for this purpose. Clinical situations where it is desirable to prevent or reduce the recruitment and/or migration of polymorphonuclear cells to a site of inflammation include, but are not limited to airway inflammation, pleurisy, myocardial infarct, cerebral infarct, stroke, reperfusion injury related to tissue or organ transplants; and reperfusion injury related to surgical intervention, embolism, wound healing, and trauma.

One aspect of the invention is the provision of novel compounds, as well as methods of their use, such as methods for preventing or reducing the recruitment and/or migration of polymorphonuclear cells to a site of inflammation in diseases of different aetiology. Other aspects of the invention, together with their advantages, will be obvious to a skilled person upon study of the claims, hereby incorporated by reference.

SHORT DESCRIPTION OF THE DRAWINGS

The invention will be disclosed in closer detail below, in the description, non-limiting examples, and claims, with reference to the enclosed drawings in which:

FIG. 1a is the prophylactic protocol in the murine model of OVA induced airway inflammation. The mice were sensitized with two i.p. injections of OVA in aluminium hydroxide gel on day 0 and 12. Treatments were performed with two intra nasal administrations of test drug or vehicle on day 16 and 21. The mice were then exposed to four aerosol challenges. The experiment was terminated on day 35.

Figure 1B:
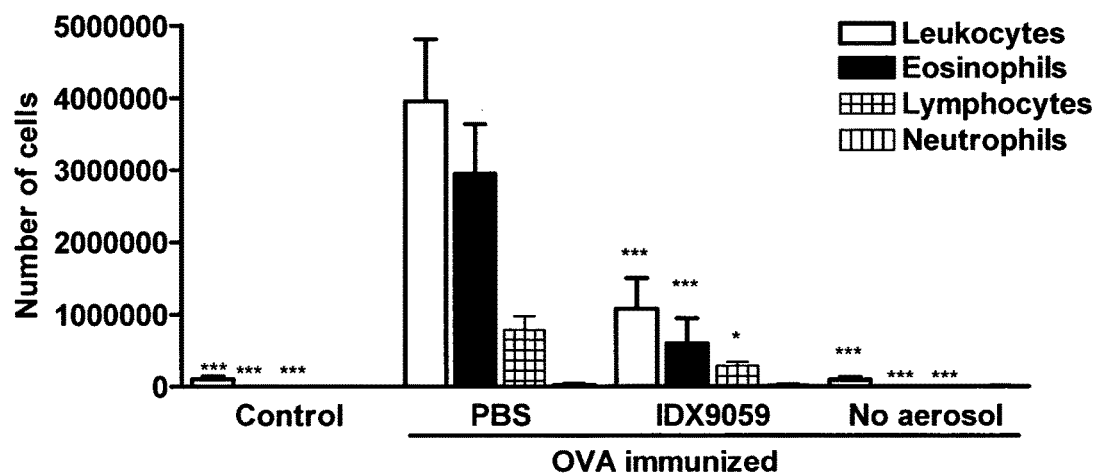

FIG. 1b is a histogram showing mean values of BAL fluid derived cells after treatment according to FIG. 1a. Treatment with IDX9059 resulted in reduction of the leukocytes, mainly eosinophils, and lymphocytes. Bar indicates mean±SD. *P<0.05, ***P<0.001 by One-way ANOVA with Bonferroni post hoc correction versus PBS control.

Figure 2A:
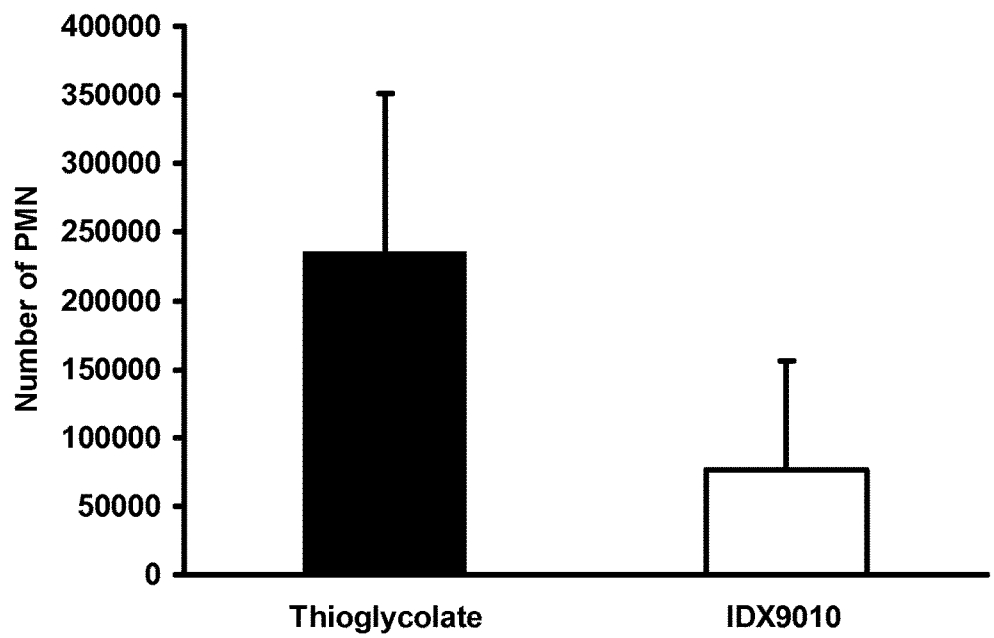
Figure 2B:
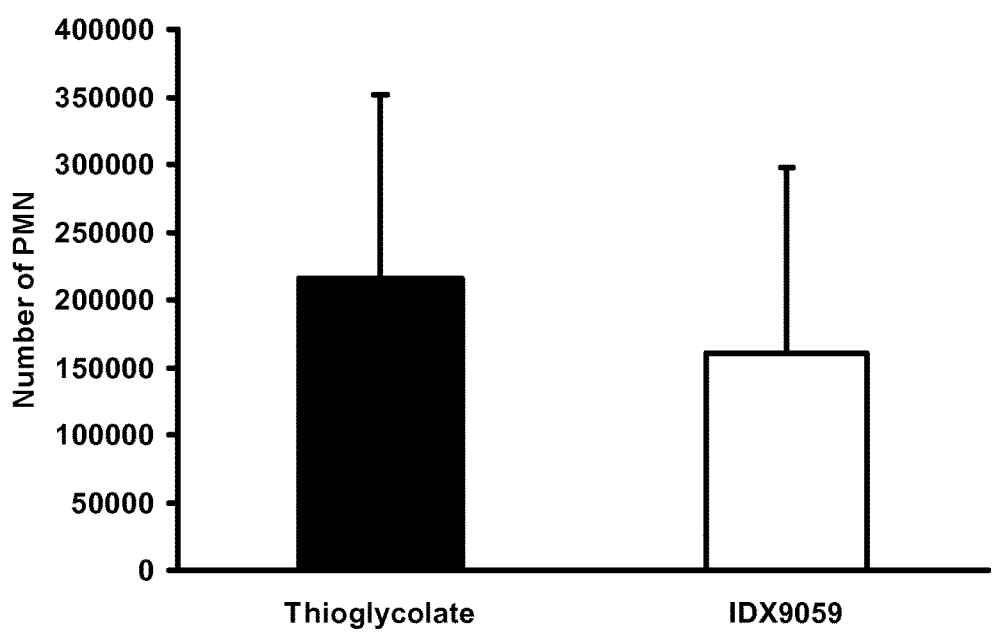

FIGS. 2a-2b show the reduction of PMN accumulation after treatment with inventive compounds in a thioglycolate induced pleurisy model in mice. FIG. 2a) IDX9010 was administered 20 minutes before induction of pleurisy and resulted in a reduction of immigrating PMN's into the pleural cavity with 68.2%. FIG. 2b) IDX9059 was administered 20 minutes before induction of pleurisy and resulted in a reduction of immigrating PMN's into the pleural cavity with 25.1%. Bars indicate mean±SD.

Figure 3A:
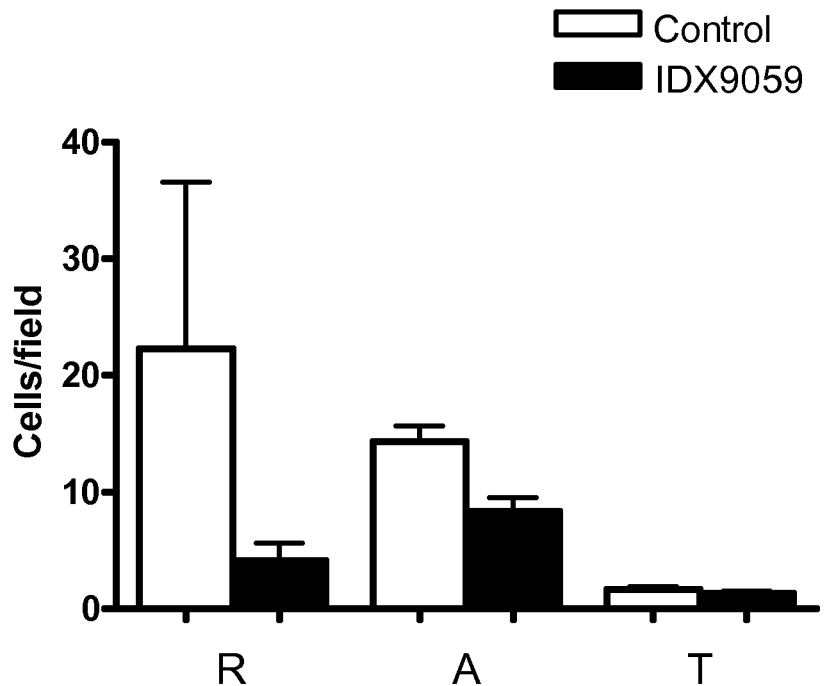

FIG. 3a is a histogram of cells per microscope field without stimulation with any chemotactic factor in a model of intravital microscopy of venules in the cremaster muscle in mice. R=rolling cells, A=adhering cells and T=transmigrated cells. n=4, mean±SD. The unstimulated cells revealed a cell activity order of R>A>T. Treatment with IDX9059 showed down regulating effects on rolling and adherence of unstimulated PMN cells.

Figure 3B:
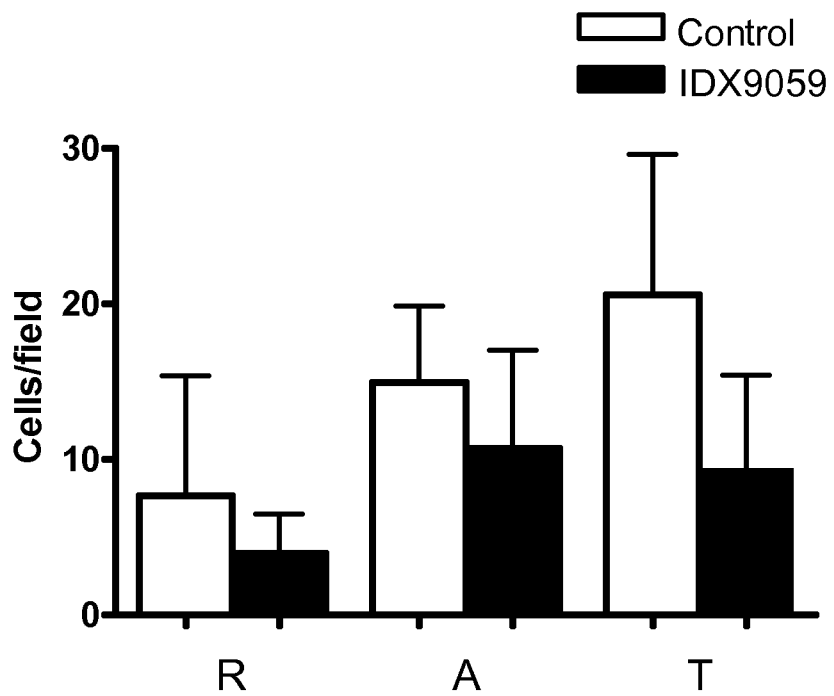

FIG. 3b is a histogram of cells per microscope field after addition of chemotactic platelet activating factor (PAF) in a model of intravital microscopy of venules in the cremaster muscle in mice. R=rolling cells, A=adhering cells and T=transmigrated cells. On stimulated cells, (after PAF) the activity order was reversed, T>A>R>. Treatment with IDX9059 showed down regulating effects on rolling and adherence of and transmigration of PMN cells. n=4, mean±SD.

FIGS. 4a-d show the effect of treatment with inventive drugs and vehicle (PBS) after induction of cerebral ischemia in rat model of focal ischemia.

4a) consists of two photographs showing a comparison of the extent of ischemic damage in non-treated animals given PBS (slide E) versus IDX9059 (slide D). The transient occlusion of middle cerebral artery was used to induce ischemic brain damage in male Wistar Hannover rats. Laser Doppler was used to show the cortical blood flow of middle cerebral artery (MCA). After 90 minutes of occlusion the filament was removed and the circulation of blood continued in the MCA and the cortical blood flow restituted. The substances were injected intraperitoneal at 0 and 24 hours after recirculation. The animals were sacrificed after 48 hours of operation and the brain removed and cut into 2 mm thick slices. The slices were then incubated in 0.8% triphenyltetrazolium chloride (TTC) in phosphate buffer to distinguish the viable brain cells (red) from necrotic (pale). The slices were photograph and the brain damage evaluated by computational analysis.

4b) is a bar diagram showing the percentage of total brain damage.

4c) is a bar diagram showing the percentage of selective nerve necrosis (SNN) area. Selective nerve necrosis is depicted as an estimation of the part that has a slightly pink tone and considered to be the penumbra region.

4d) is a bar diagram showing the percentage of infarct region (ischemic core). Data shown as mean±SD (n=4-8). Mean indicated with bar. *P<0.05 obtained by unpaired t-test in treated group versus PBS control.

Figure 5:
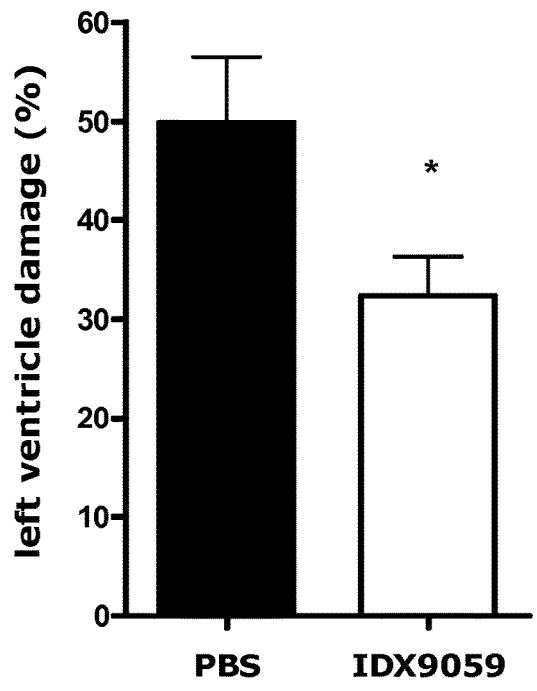

FIG. 5 is a bar diagram showing the percentage of infarct in an animal model of heart ischemia. IDX9059 (1 µg/µl) or placebo was given (100 µl) subcutaneously 24 hrs before excision of the heart. The hearts were harvested and perfused for 20 minutes for stabilization. Global ischemia was induced by stopping perfusion, followed by 120 minutes of reperfusion. At the end of reperfusion the heart was removed and the left ventricle was cut into four slices, each of one mm thick and were incubated in 1% triphenyltetrazolium chloride in phosphate buffer to distinguish the viable cardiomyocytes. Photographs were taken from the slices and the infarct volume evaluated by computational analysis. The results are shown in a bar diagram showing the percentage of infarct damage. The data show mean (n=8) and SEM. *P<0.05 was calculated by Mann-Whitney test.

Figure 6A:
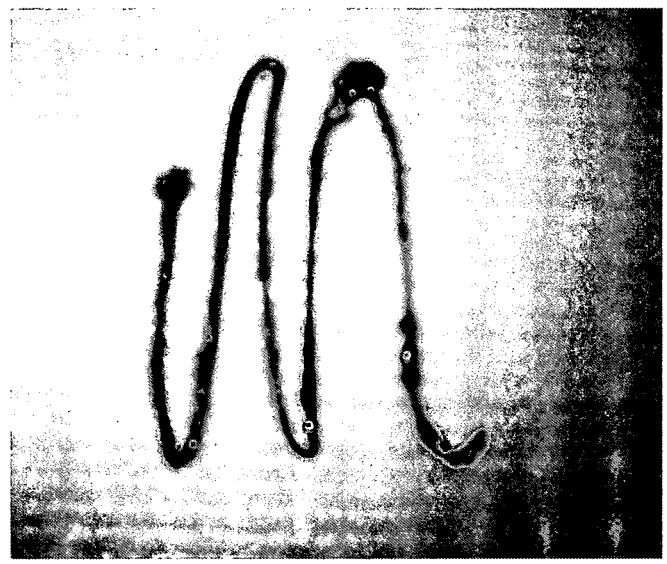
Figure 6B:
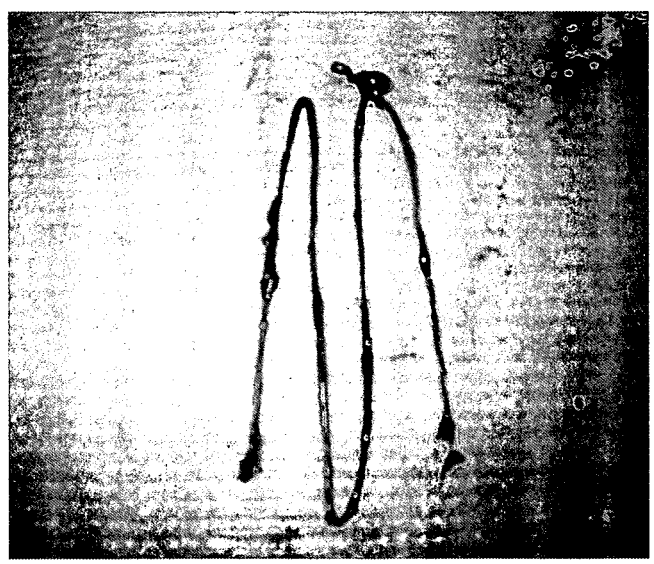
Figure 6C:
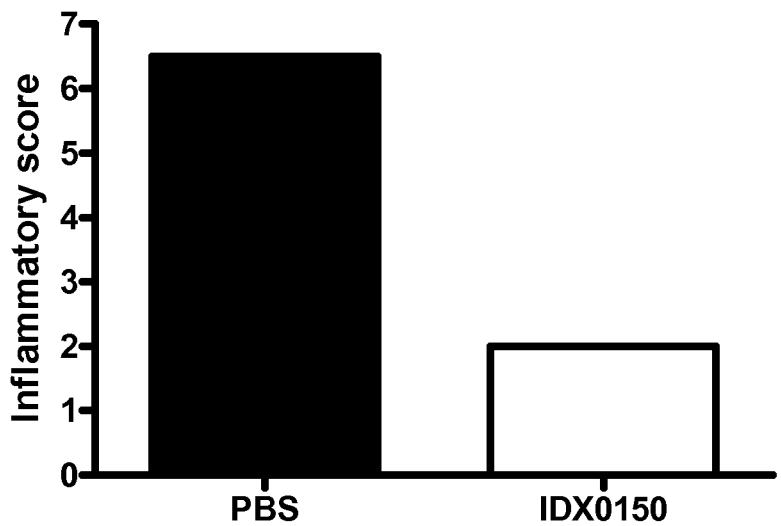
Figure 6D:
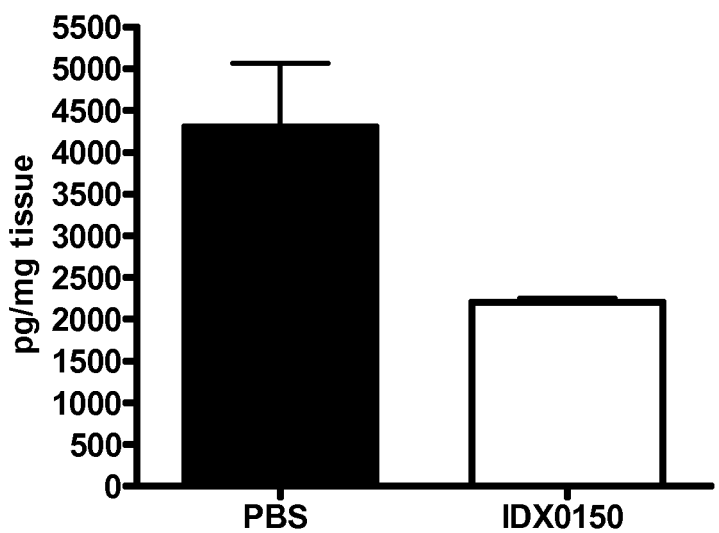

FIGS. 6a-c show result of treatment with IDX0150 and vehicle (PBS) in a mouse model of intestinal ischemia-reperfusion. The ischemia was induced by 15 minutes ligation of mesentric artery followed by 3 hours of reperfusion. The mouse received PBS (6a), or IDX0150 (6b) 20 minutes before induction of ischemia. 6a-b) illustrate part of mouse digestive tract (stomach, left; small intestine; caecum and colon) after administration of PBS or IDX0150, respectively. The inflammatory score of mice treated with the IDX0150 (score 2) versus mice receiving PBS (score 6.5) is shown in 6c.

FIGS. 6d-g show the levels of myeloperoxidase (MPO) in intestinal and lung tissue in the mouse model of intestinal ischemia and reperfusion injury. IDX0150 or PBS was administered subcutaneously 20 min before induction of ischemia (6d, and 6f) or immediately after start of reperfusion (6e, and 6g). After 3 h of reperfusion, small intestine (6d, and 6e) and lungs (6f, and 6g) were homogenized and the levels of MPO were analyzed with ELISA. Results are presented as mean values with standard deviations.

FIGS. 7a-f show the results of CXCR1 and CXCR2 expression on human peripheral PMN after stimulation with different test substances. Human PMN from 5 healthy blood donors were stimulated with 25 µM of test compounds or with medium alone (untreated) for 3 h. Cells were subsequently harvested and analyzed for CXCR1 and CXCR2 expression by flow cytometry. The fold changes in mean fluorescence intensity (MFI) for CXCR1 (7a) and CXCR2 (7c) or the fold changes in the % of CXCR1+ (7b) and CXCR2+ (7d) CD66b+ PMN were calculated by normalizing the MFI or % positive PMN of corresponding untreated cells to 1 (dotted black line). 7e) illustrates the relative MFI of CXCR1+ PMN after stimulation with 0.5, 10 and 25 µM of IDX9052, IDX9054 and IDX9059 (n=5). 7f) shows the relative MFI of CXCR1+ PMN after stimulation with 10 µM IDX9074 in a separate experiments using PMN from 5 healthy blood donors. Results are presented as mean±SEM. *P<0.05, P<0.01 and *P<0.001 were calculated by two-way ANOVA with Bonferroni's post hoc correction versus untreated cells.

Figure 7A:
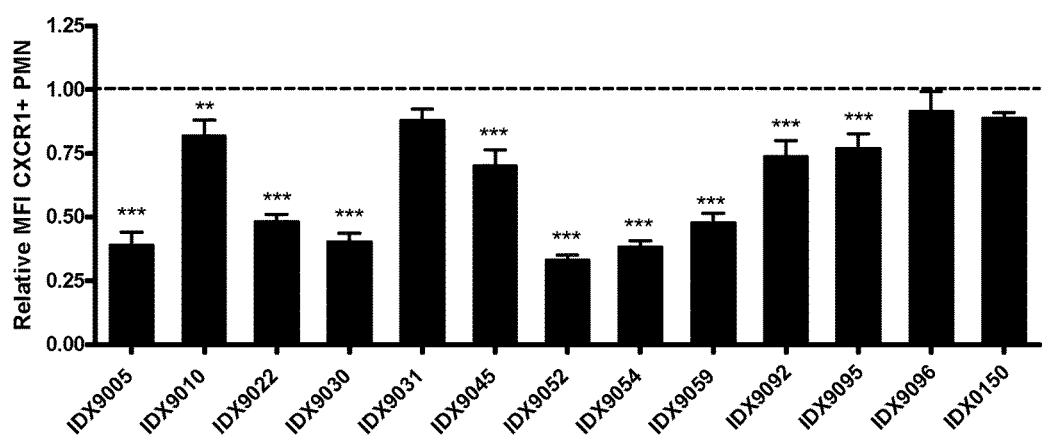
Figure 7B:
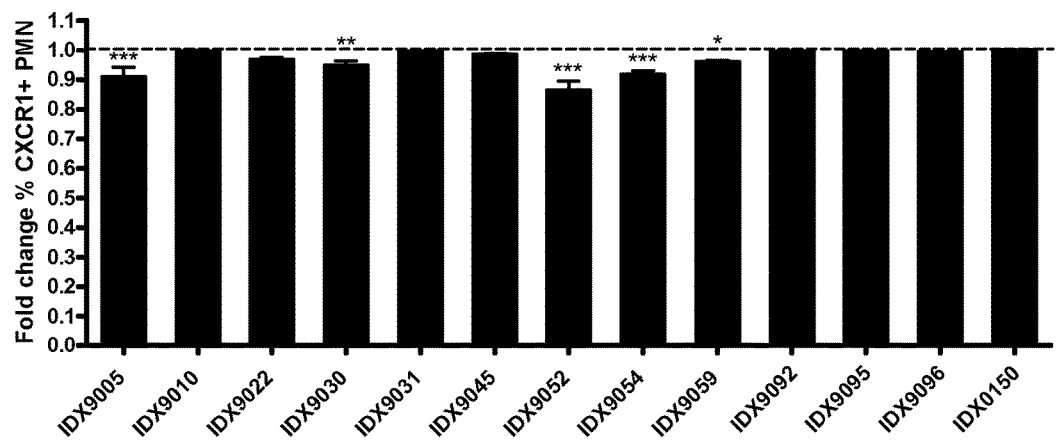
Figure 7C:
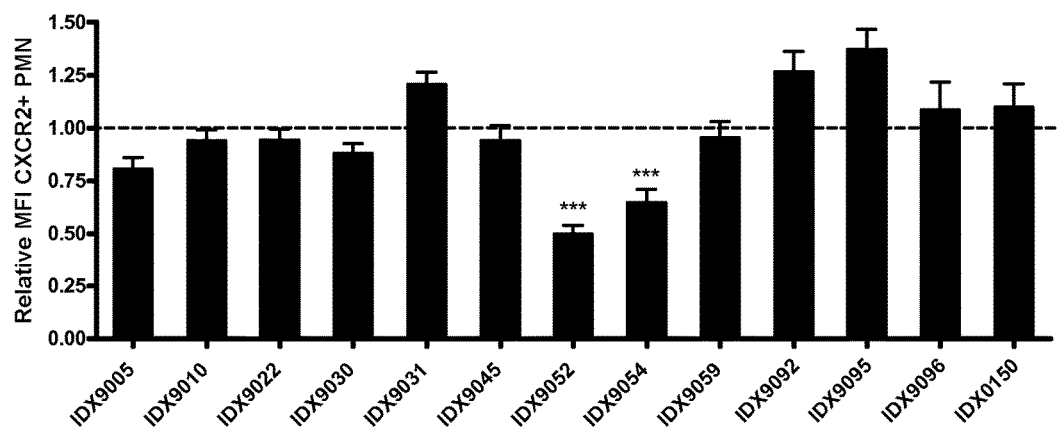
Figure 7D:
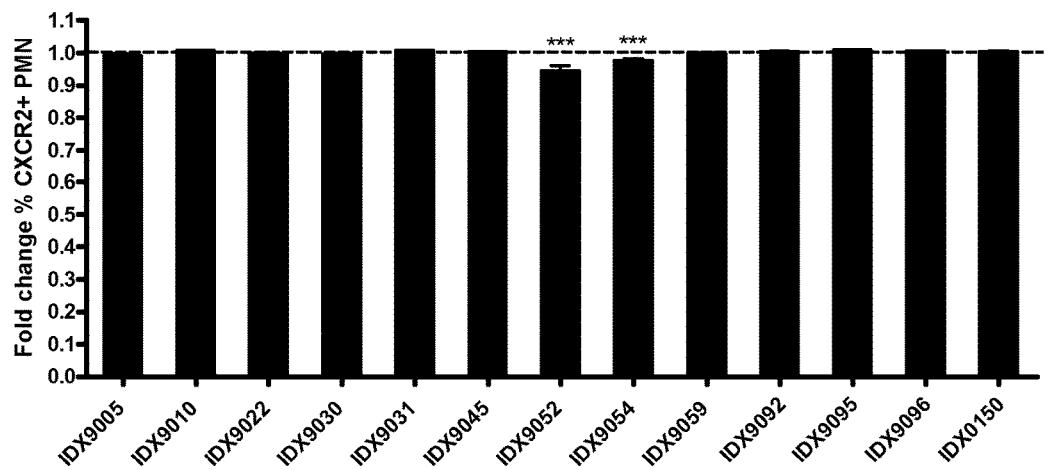
Figure 7E:
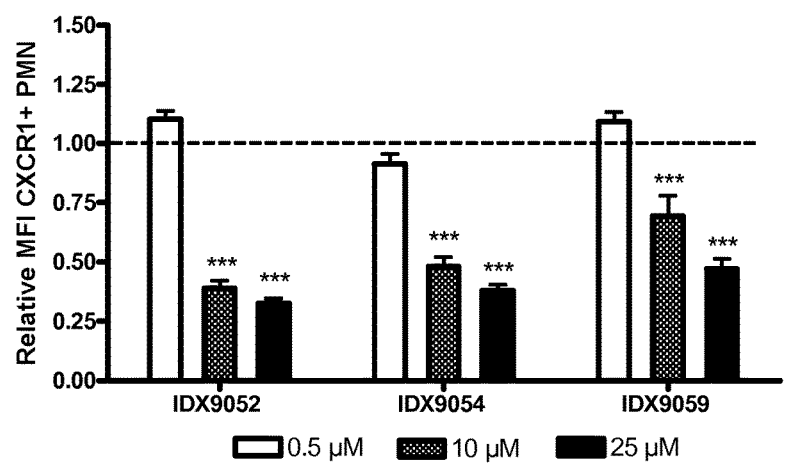
Figure 7F:
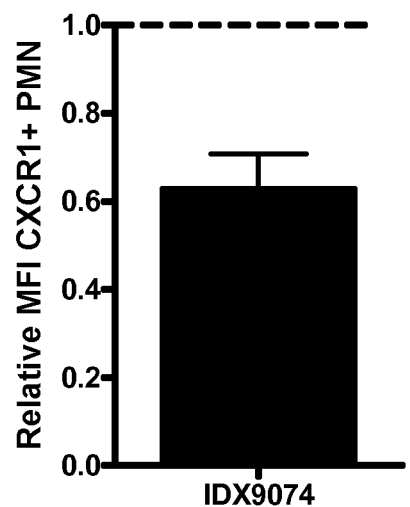
Figure 7G:
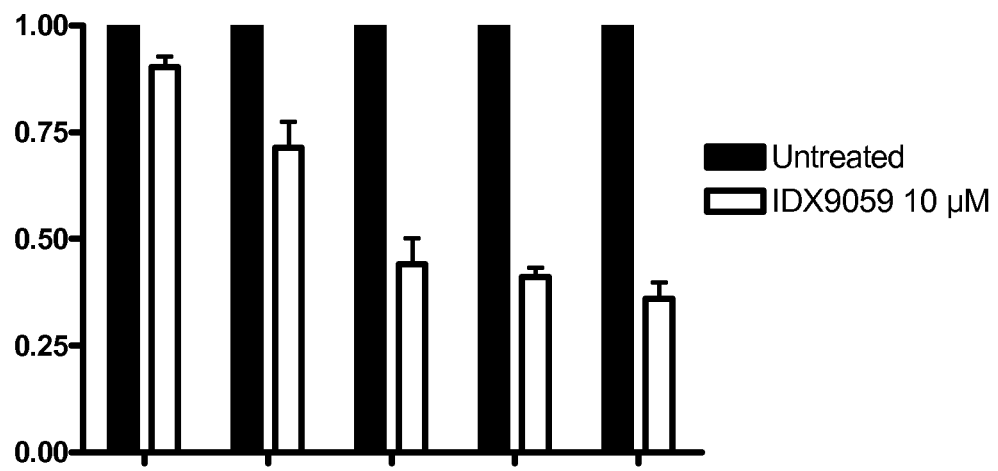

FIG. 7g illustrates CXCR1 expression on human PMN stimulated with IDX9059 for various time points. Human PMN from 3 healthy blood donor were stimulated with 10 µM of IDX9059 for 15 min, 30 min, 1 h, 2 h or 3 h. Cells were subsequently harvested and fixated at each time point and analyzed for CXCR1 expression by flow cytometry. The fold changes in MFI of CXCR1 of CD66b positive PMN in IDX9059 treated cells were calculated by normalizing the MFI of corresponding untreated cells to 1. Results are presented as mean values±SEM.

Figure 7H:
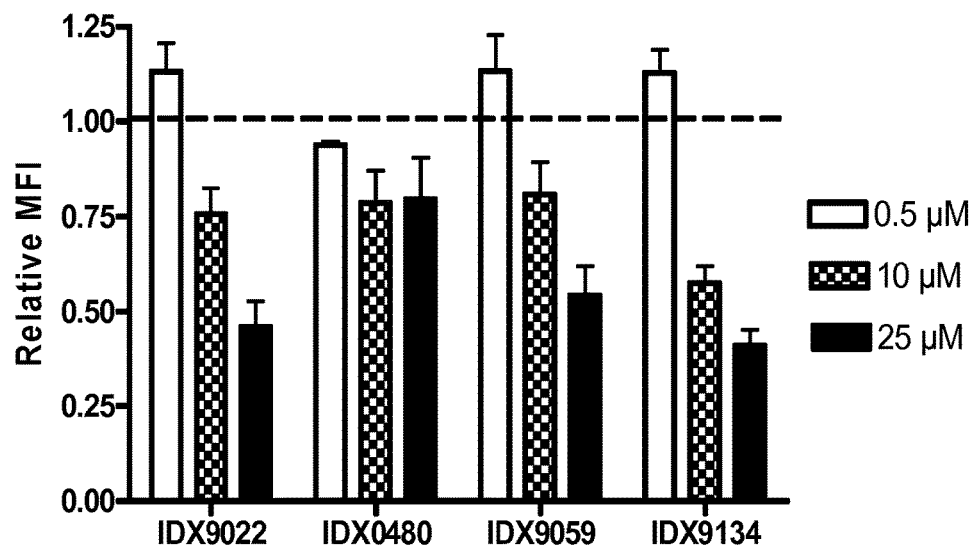

FIG. 7h shows the importance of CpG and oligo G-oligonucleotides on the surface expression of CXCR1. Human PMN from 3 healthy blood donors were incubated for 3 h with 0.5, 10 or 25 µM of IDX9022 and IDX9059 as well as the modified control oligonucleotides IDX0480 and IDX9134, which have the same sequences as IDX9022 and IDX9059, respectively, but without CpG motifs. Cells were subsequently harvested and analyzed for CXCR1 expression by flow cytometry. The fold changes in MFI of CXCR1+ CD66b+ PMN were calculated by normalizing the MFI of untreated cells to 1 (dotted black line). Results are presented as mean±SEM.

Figure 7I:
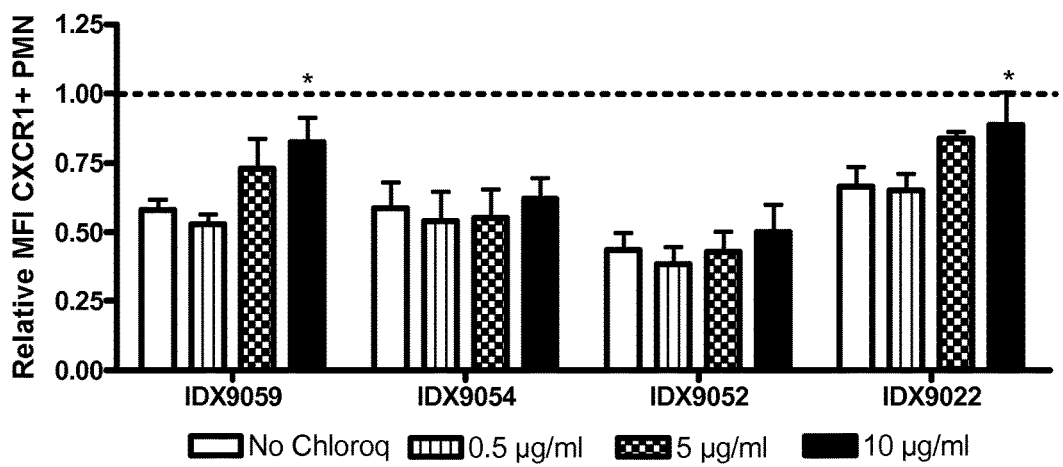

FIG. 7i demonstrates the effect of chloroquine on down-regulation of CXCR1 surface expression after treatment with inventive compounds. Human PMN from 4 healthy blood donors were pre-incubated for 30 min with 0.5, 5 or 10 µg/ml of chloroquine before stimulated with 10 µM of test compounds for 3 h. Cells were subsequently harvested and analyzed for CXCR1 expression by flow cytometry. The fold changes in MFI were calculated by normalizing the MFI of corresponding untreated cells to 1 (dotted black line). Results are presented as mean±SEM. *P<0.05 was calculated by two-way ANOVA with Bonferroni's post hoc correction versus untreated cells.

Figure 7J:
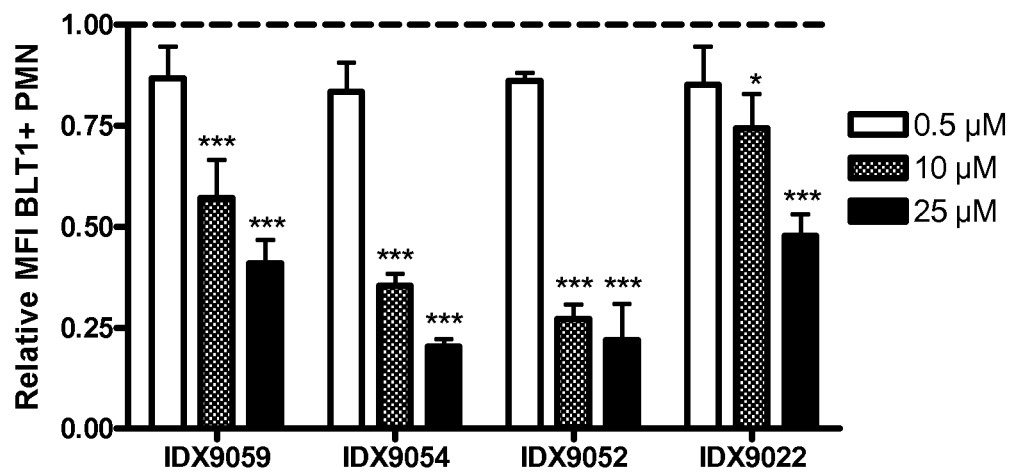
Figure 7K:
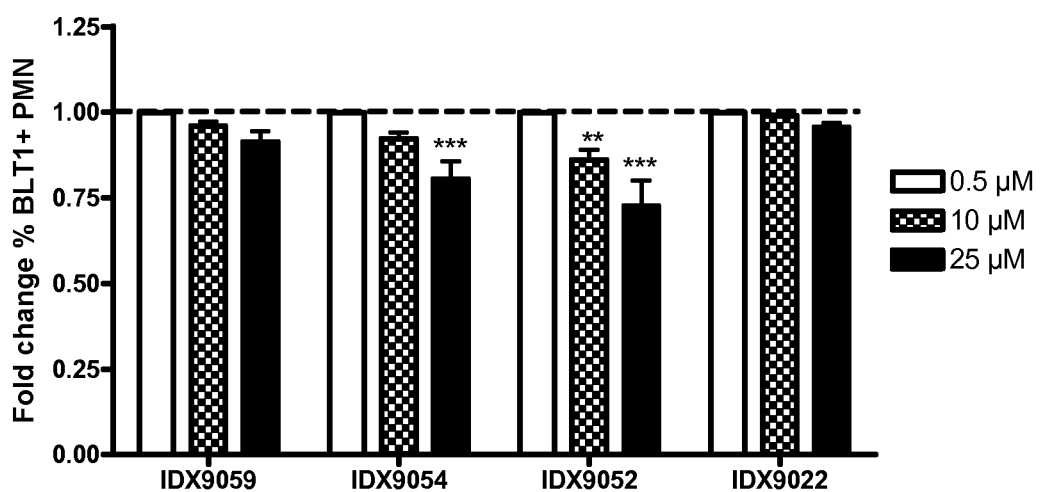

FIGS. 7j-k show the results of BLT1 surface expression on human PMN after stimulation with different test substances. Human PMN from 5 healthy blood donors were stimulated with 0.5, 10 or 25 µM of inventive compounds or with medium alone (untreated) for 3 h. Cells were subsequently harvested and analyzed for BLT1 expression by flow cytometry. The fold change in MFI (7j) or % BLT1+CD66b positive PMN (7k) were calculated by normalizing the MFI or % of corresponding untreated cells to 1 (dotted black line). Results are presented as mean and SEM. *P<0.05, P<0.01 and *P<0.001 were calculated by two-way ANOVA with Bonferroni's post hoc correction versus untreated cells.

Figure 7L:
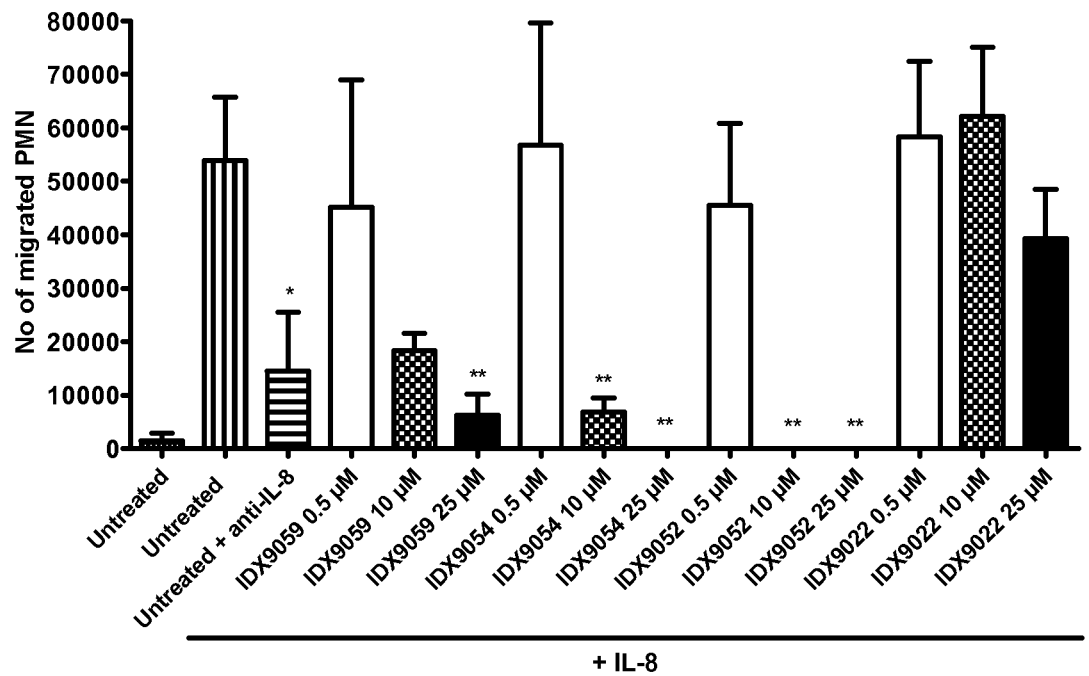
Figure 7M:
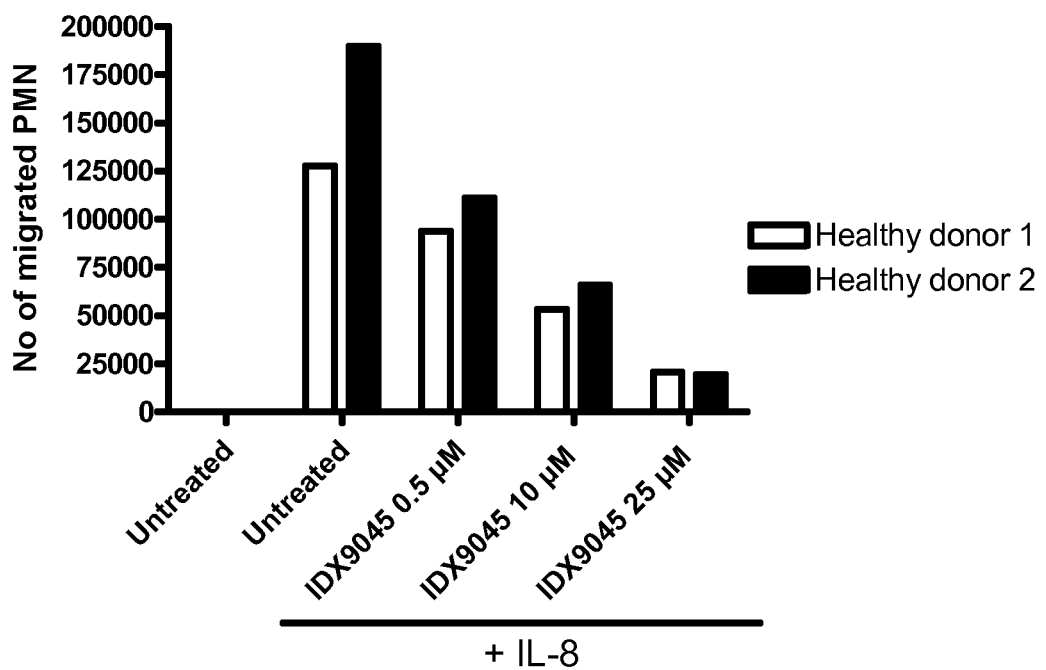
Figure 7N:
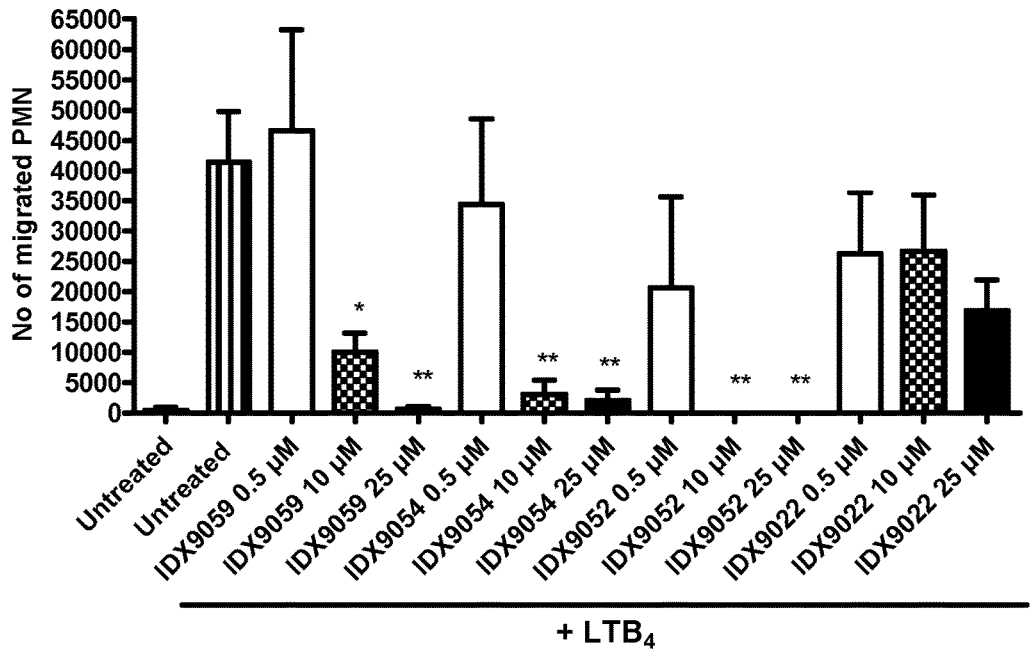

FIG. 7l-n show the effect of the inventive compounds on IL-8 and $LTB_4$ induced chemotaxis of PMN. Human PMN from 5 (7l) or 4-6 (7n) healthy blood donors were preincubated with 0.5, 10 or 25 μM of inventive compounds for 1 h after which free compound were washed away and the cells were investigated for their ability to migrate towards IL-8 (7l) or LTB$_4$ (7n) in a chemotaxis assay for 3 h. Results are presented as the mean number of migrated PMN±SEM. *P<0.05 and **P<0.01 were calculated by one-way ANOVA with Dunnett's post hoc correction versus untreated cells incubated with IL-8/LTB$_4$. 7m) shows a separate experiment where PMN from 2 healthy blood donors were preincubated with 0.5, 10 or 25 μM of IDX9045 for 1 h, after which the cells were investigated for their ability to migrate towards IL-8 in the presence of free compound in a chemotaxis assay for 3 h.

Figure 7O:
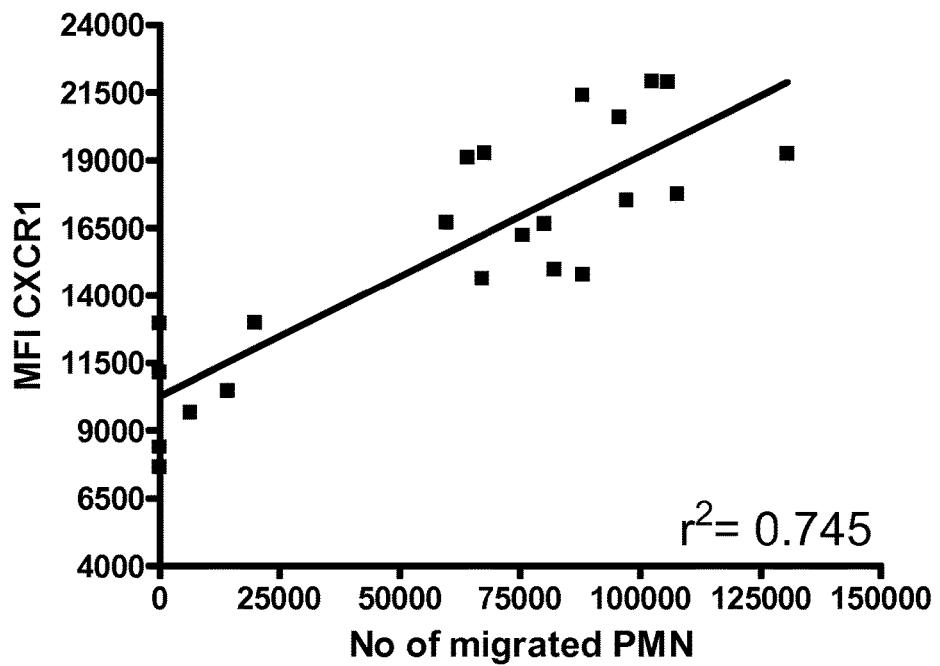
Figure 7P:
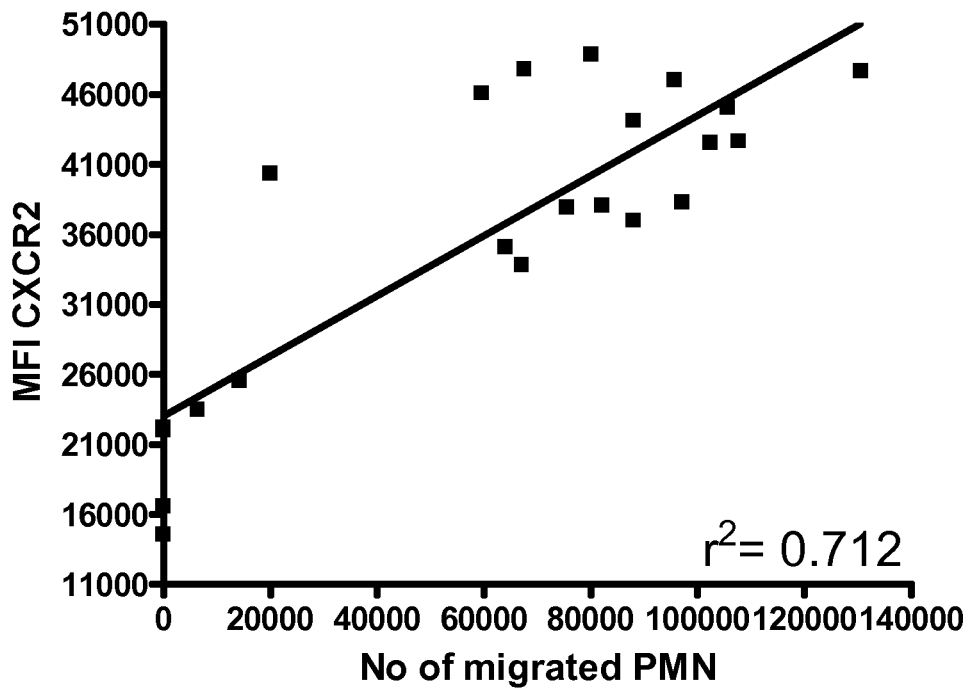
Figure 7Q:
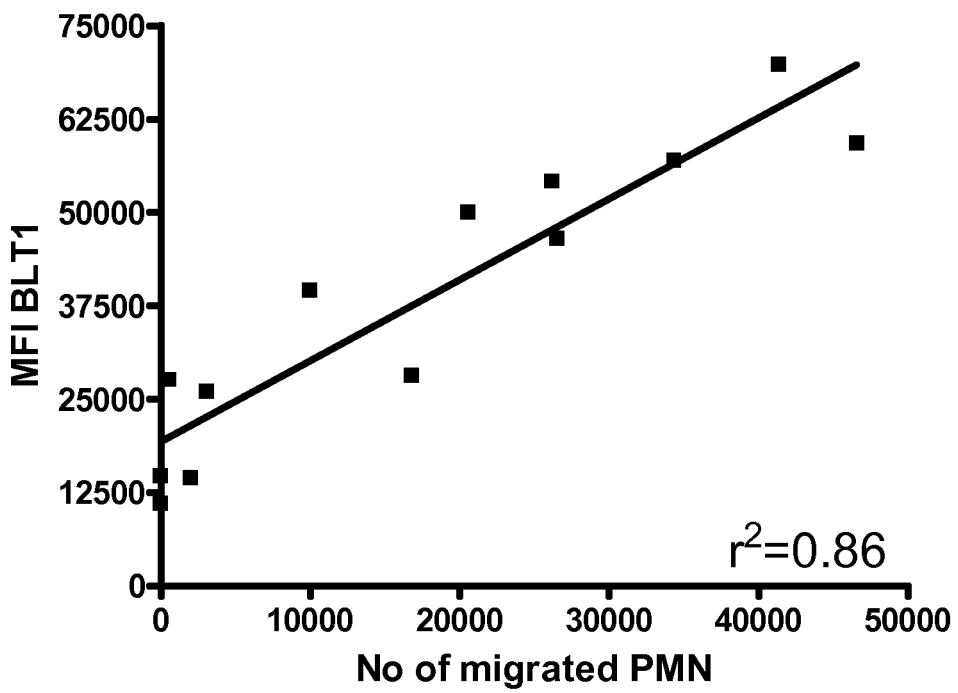

FIG. 7o-q demonstrate the correlation between CXCR1, CXCR2 and BLT1 surface expression and PMN migration after stimulation with the inventive compounds. The MFI of CXCR1 (7o), CXCR2 (7p) and BLT1 (7q) of PMN after stimulation with inventive compounds were plotted against the number of PMN that migrated towards IL-8 (7o and 7p) or LTB$_4$ (7q) in the chemotaxis assay. The curve fit ($r^2$) is specified in the figures.

FIG. 8a-f show the results of CXCR1, CXCR2 and BLT1 expression on human peripheral PMN isolated from MS patients after stimulation with different test substances. Human PMN from MS patients were stimulated with 0.5, 10 and 25 μM of test compounds or with medium alone (untreated) for 3 h. Cells were subsequently harvested and analyzed for CXCR1 (n=4), CXCR2 (n=4) and BLT1 (n=2) expression by flow cytometry. The fold changes in mean fluorescence intensity (MFI) for CXCR1 (8a), CXCR2 (8c) and BLT1 (8e) or the fold changes in the % of CXCR1+ (8b), CXCR2+ (8d) and BLT1+ (8f) CD66b+ PMN were calculated by normalizing the MFI or % positive PMN of corresponding untreated cells to 1 (dotted black line). Results are presented as mean±SEM. *P<0.05, P<0.01 and *P<0.001 were calculated by two-way ANOVA with Bonferroni post hoc correction versus untreated cells.

Figure 8A:
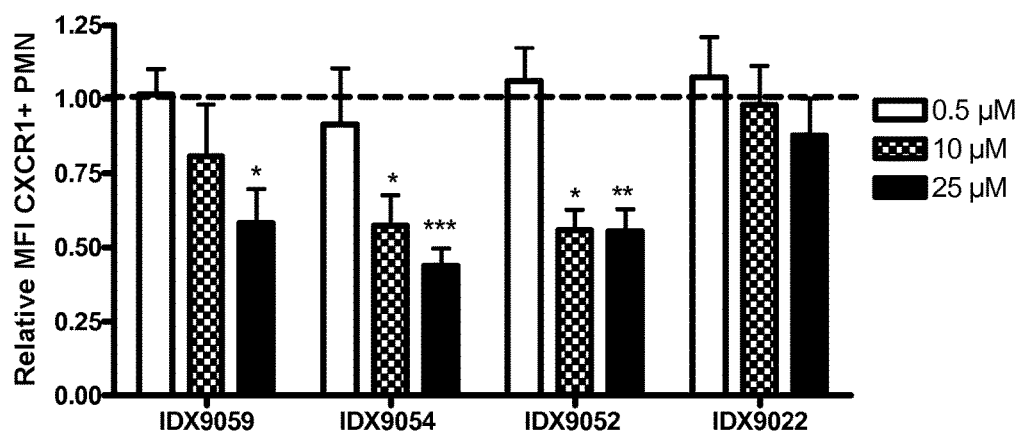
Figure 8B:
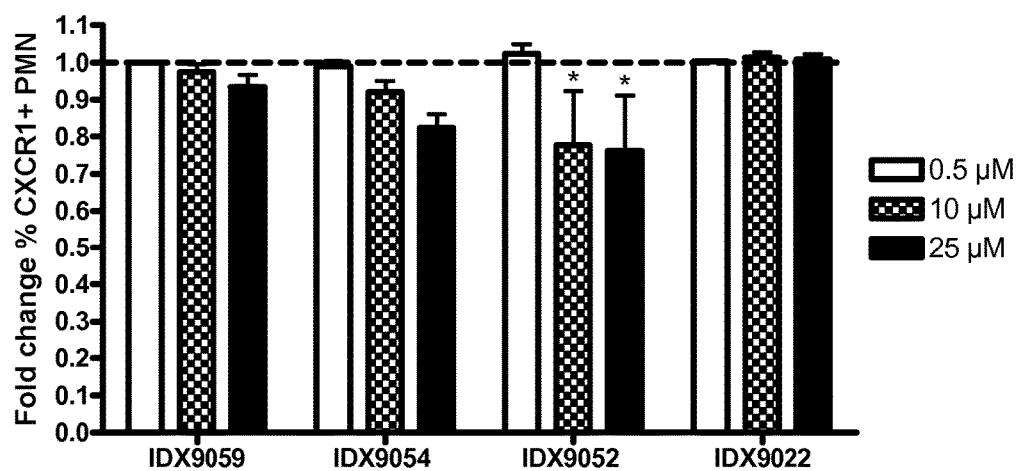
Figure 8C:
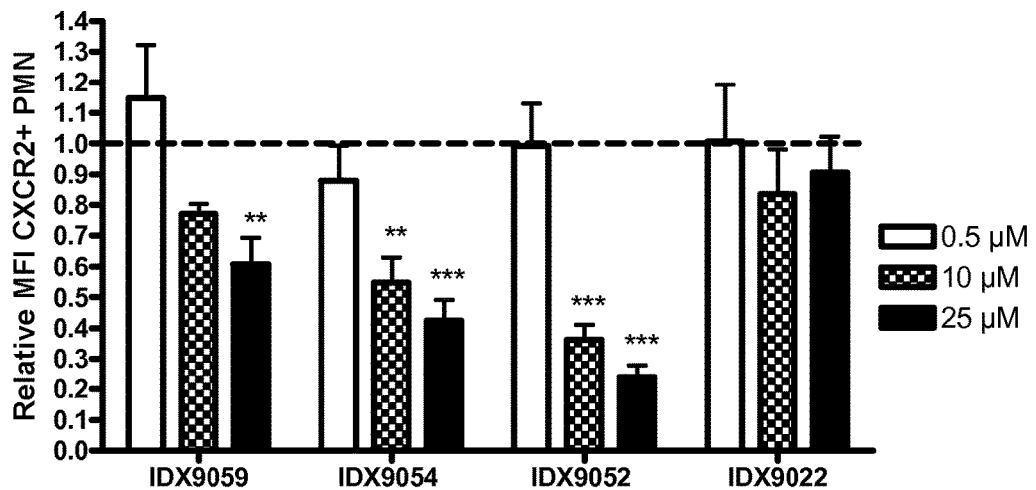
Figure 8D:
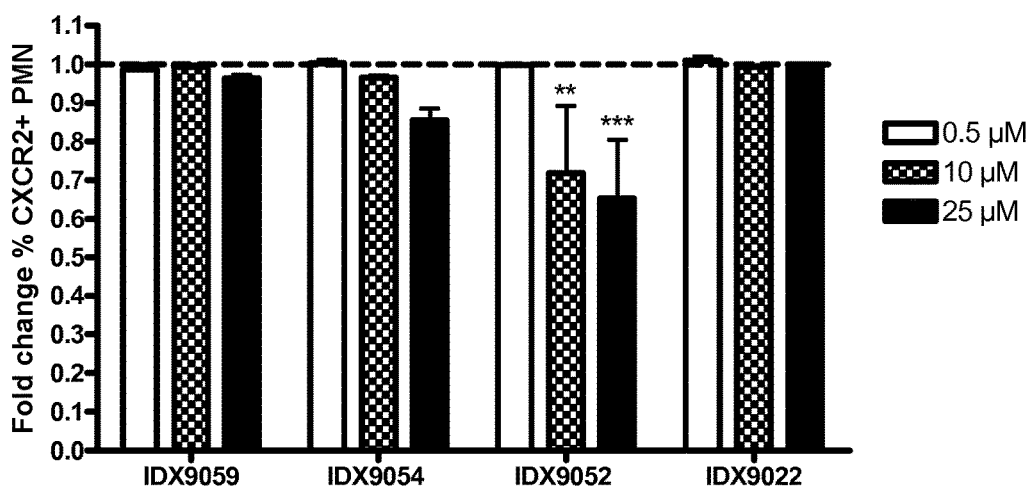
Figure 8E:
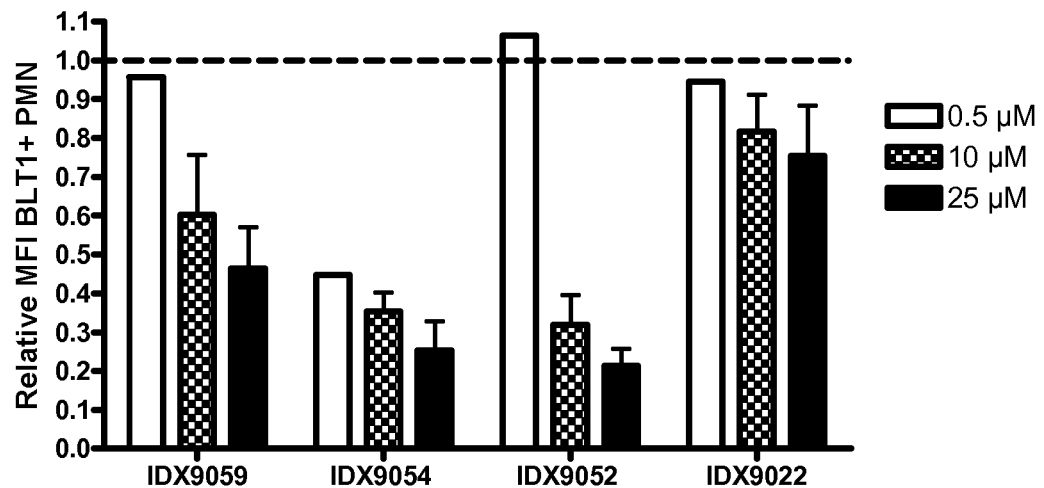
Figure 8F:
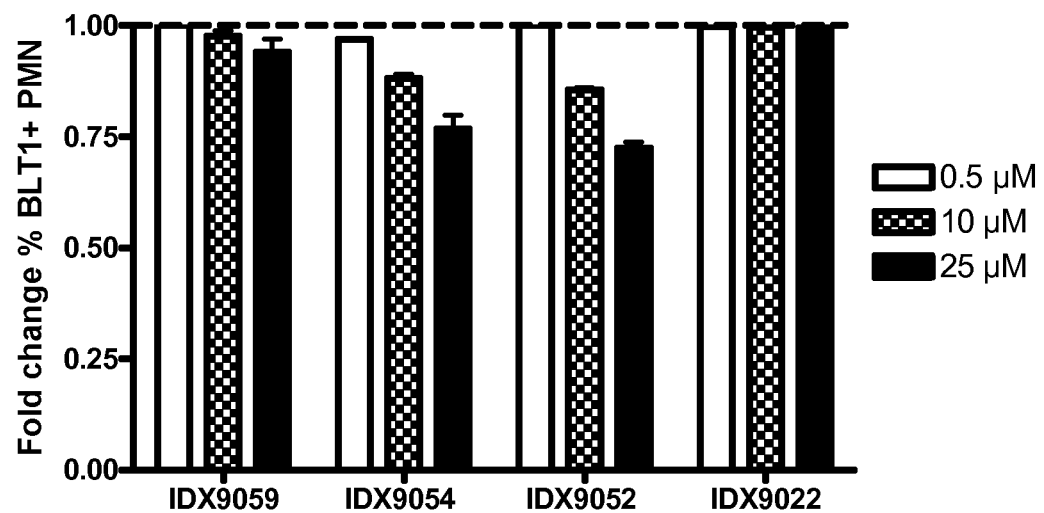
Figure 8G:
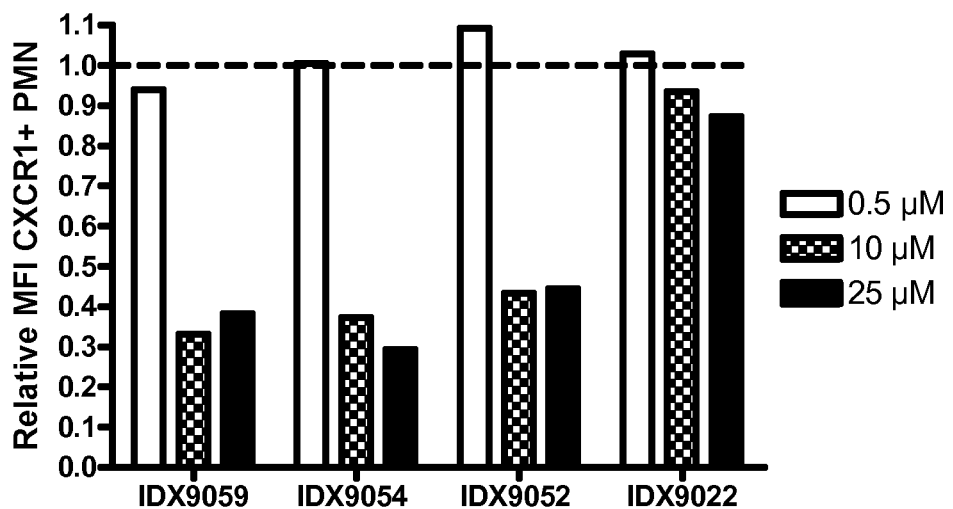
Figure 8H:
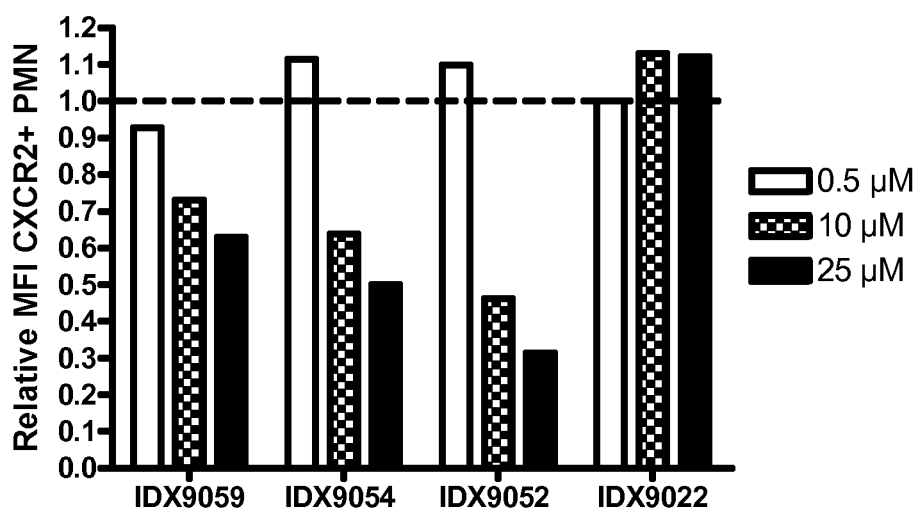
Figure 8I:
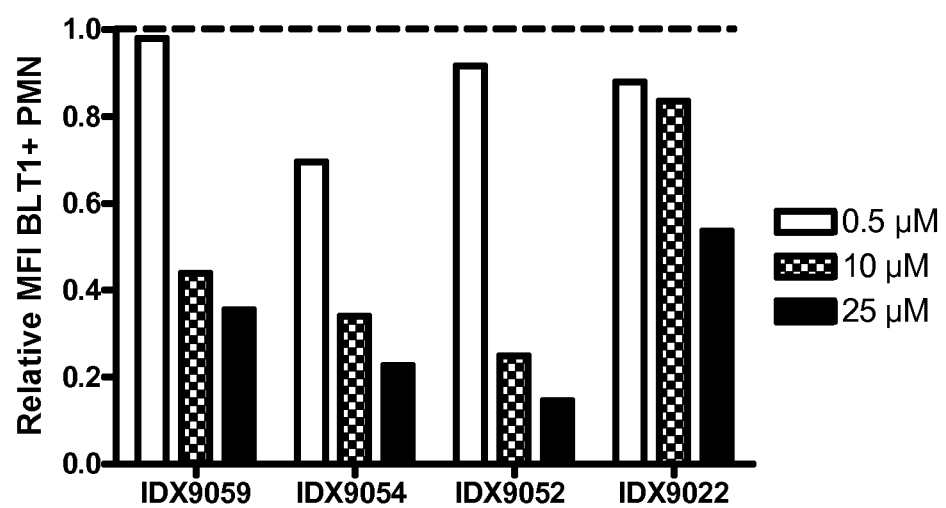

FIG. 8g-i illustrate the results of CXCR1, CXCR2 and BLT1 expression on human peripheral PMN derived from an asthmatic patient after stimulation with the inventive compounds. Human PMN from an asthmatic patient were stimulated with 0.5, 10 and 25 μM of test compounds or with medium alone (untreated) for 3 h. Cells were subsequently harvested and analyzed for CXCR1, CXCR2 and BLT1 expression by flow cytometry. The fold changes in mean fluorescence intensity (MFI) for CXCR1 (8g), CXCR2 (8h) and BLT1 (8i) CD66b+ PMN were calculated by normalizing the MFI of corresponding untreated cells to 1 (dotted black line).

DETAILED DESCRIPTION

Before the present invention is described, it is to be understood that the terminology employed herein is used for the purpose of describing particular embodiments only and is not intended to be limiting, since the scope of the present invention will be limited only by the appended claims and equivalents thereof.

It must be noted that, as used in this specification and the appended claims, the singular forms "a," "an," and "the" include plural referents unless the context clearly dictates otherwise.

Also, the term "about" is used to indicate a deviation of +/−2% of the given value, preferably +/−5%, and most preferably +/−10% of the numeric values, where applicable.

In addition to the above, the following terms will be used:

The term "homology" and "degree of homology" means the similarity or identity between two sequences, where 100% homology means that the sequences are identical, and a lower homology indicates the presence of variations. For example, for a sequence consisting of 20 nucleobases, another sequence is 90% homologous if 18 bases are the same.

"Functionally homologous" means sequences sharing perhaps a lower structural homology with the disclosed sequence, but exhibiting homologous function in vivo, in either the healthy or the diseased organism, e.g. coding the same or highly similar proteins with similar cellular functions.

The terms "treatment", "therapy", "therapeutic use", "medicament", and "medical use" encompass both human and animal or veterinary applications.

The present inventors have found that specific oligonucleotides are capable of influencing the properties and behaviour of polymorphonuclear cells, e.g. their endothelial adhesion and transmigration, and that these compounds through this and possibly other mechanisms have utility in the prevention and/or alleviation of diseases of different etiology. These findings have been confirmed in animal experiments and in in vitro tests performed on PMNs isolated from donor blood.

| SEQ ID NO | | |
|---|---|---|
| IDX9005 | T*C*G*TCCATGGTCA GGGTCCCGG*G*G*G |
| IDX9010 | T*C*C*CAAGAGTCGTCC*A*G*G |
| IDX9022 | T*C*G*TCGTTCTGCCATCGTC*G*T*T |
| IDX9030 | T*C*G*TCTGCCATGGCGGCC*G*C*C |
| IDX9031 | T*C*G*TCGATTCGTCTGCCA*T*G*G |
| IDX9045 | G*G*G*TCGCAGC*T*G*G |
| IDX9054 | G*G*G*GTCGTCTGC*G*G*G |
| IDX9059 | G*A*T*CGTCCG*G*G*G |
| IDX9074 | T*C*G*TTCGTCTTTCGTC*T*G*C |
| IDX9092 | T*T*T*CGTCTGCTTTCGTTTCG*T*T*T |
| IDX9095 | T*C*G*TCTGCTTTCGTC*T*G*C |
| IDX9096 | G*A*T*CGTCCGATCG*T*C*C |
| IDX0150 | G*G*A*ACAGTTCGTCCAT*G*G*C |
| IDX9052 | G*G*G*GTCGTCTG*C*G*G |
| IDX0480 | T*<u>G*C</u>*TGCTTCTGCCAT<u>GCTG*C</u>*T*T |
| IDX9134 | G*A*T*<u>GCTCTG</u>*G*G*G |

The inventors make available novel oligonucleotides, and accordingly one embodiment of the invention is an isolated and substantially purified oligonucleotide chosen from the group consisting of SEQ ID NO 1-12, 14, 15, and 16, and in particular SEQ ID NO 8 [IDX9059]; SEQ ID NO 14 [IDX9052]; SEQ ID NO 7 [IDX9054]; SEQ ID NO 6 [IDX9045]; SEQ ID NO 1 [IDX9005]; SEQ ID NO 9 [IDX9074]; SEQ ID NO 3 [IDX9022]; SEQ ID NO 2 [IDX9010]; and SEQ ID NO 4 [IDX9030].

Preferably at least one nucleotide in a sequence chosen from the sequences above has a phosphate backbone modification. Said phosphate backbone modification is preferably a phosphorothioate or phosphorodithioate modification.

The inventors also make available a pharmaceutical composition comprising an oligonucleotide chosen from the sequences above.

One embodiment of the invention is the use of an oligonucleotide for the production of a pharmaceutical preparation for reducing the recruitment and/or migration of polymorphonuclear cells to a site of inflammation, wherein the oligonucleotide is chosen from the group consisting of: SEQ ID NO 8 [IDX9059]; SEQ ID NO 14 [IDX9052]; SEQ ID NO 7 [IDX9054]; SEQ ID NO 6 [IDX9045]; SEQ ID NO 1 [IDX9005]; SEQ ID NO 9 [IDX9074]; SEQ ID NO 3 [IDX9022]; SEQ ID NO 2 [IDX9010]; SEQ ID NO 4 [IDX9030]; and SEQ ID NO 13 [IDX0150].

Preferably, according to the results currently available to the inventors, said reduced recruitment and/or migration of polymorphonuclear cells to a site of inflammation is a result of a down-regulation of at least one of the receptors CXCR1 and CXCR2, or a result of a down-regulation of the receptor BLT1.

According to a preferred embodiment, said oligonucleotide is preferably chosen among: SEQ ID NO. 8 [IDX9059]; SEQ ID NO. 14 [IDX9052]; and SEQ ID NO. 7 [IDX9054].

In the above use, the oligonucleotide is preferably given through one of the following routes of administration: subcutaneous, intraperitoneal, mucosal, intestinal, oral, gastric, oesophagal, buccal, nasal, and pulmonary administration.

According to a preferred embodiment, freely combinable with the above, the oligonucleotide is administered as a step in the treatment of an inflammatory disease.

According to another preferred embodiment, freely combinable with the above, the oligonucleotide is administered to a patient having suffered from, or suspected to have suffered from, a myocardial infarct.

According to another preferred embodiment, freely combinable with the above, the oligonucleotide is administered to a patient having suffered from, or suspected to have suffered from, a stroke.

According to another preferred embodiment, freely combinable with the above, the oligonucleotide is administered to a patient having suffered from trauma or burn, or scheduled to undergo surgery.

According to another preferred embodiment, freely combinable with the above, the oligonucleotide is administered to a patient having an embolism before removal of the embolism or before administration of a thrombolytic agent. As the compounds have been shown to have also a post-conditioning effect, it is contemplated that they are administered also after the removal of the embolism or administration of a thrombolytic agent, something that significantly increases their usefulness in an intensive care setting.

According to another preferred embodiment, freely combinable with the above, the oligonucleotide is administered to an organ designated for transplantation, either in situ, before extraction from the donor, in transit before implantation in the recipient, or in vivo, before or at the time of restoring the blood flow.

Further, the inventors make available a method for reducing the recruitment and/or migration of polymorphonuclear cells to a site of inflammation in an organ of a human patient, wherein the oligonucleotide chosen from the group consisting of: SEQ ID NO 8 [IDX9059]; SEQ ID NO 14 [IDX9052]; SEQ ID NO 7 [IDX9054]; SEQ ID NO 6 [IDX9045]; SEQ ID NO 1 [IDX9005]; SEQ ID NO 9 [IDX9074]; SEQ ID NO 3 [IDX9022]; SEQ ID NO 2 [IDX9010]; SEQ ID NO 4 [IDX9030]; and SEQ ID NO 13 [IDX0150], is administered locally to said organ or systemically to said patient.

Alternatively, the inventors make available a method for reducing the recruitment and/or migration of polymorphonuclear cells to a site of inflammation in an organ, wherein an oligonucleotide is administered locally to said organ or systemically to said patient before, simultaneously with, or after reperfusion of said organ, wherein the oligonucleotide is chosen from the group consisting of: SEQ ID NO 8 [IDX9059]; SEQ ID NO 14 [IDX9052]; SEQ ID NO 7 [IDX9054]; SEQ ID NO 6 [IDX9045]; SEQ ID NO 1 [IDX9005]; SEQ ID NO 9 [IDX9074]; SEQ ID NO 3 [IDX9022]; SEQ ID NO 2 [IDX9010]; SEQ ID NO 4 [IDX9030]; and SEQ ID NO 13 [IDX0150].

In either of the above methods of treatment, and according to the results currently available to the inventors, said reduced recruitment and/or migration of polymorphonuclear cells to a site of inflammation is a result of a down-regulation of at least one of the receptors CXCR1 and CXCR2, or a result of a down-regulation of the receptor BLT1.

In the above methods of treatment, said oligonucleotide is preferably chosen among: SEQ ID NO. 8 [IDX9059]; SEQ ID NO. 14 [IDX9052]; and SEQ ID NO. 7 [IDX9054].

The inventors also contemplate a method for conditioning a patient having suffered or suspected of having suffered from a disturbance or interruption in the blood flow in an organ and scheduled for treatment, wherein an oligonucleotide capable of reducing the recruitment and/or migration of polymorphonuclear cells to a site of inflammation in said organ, is administered to said patient before, simultaneously with, or after the scheduled treatment, wherein the oligonucleotide is chosen from the group consisting of: SEQ ID NO 8 [IDX9059]; SEQ ID NO 14 [IDX9052]; SEQ ID NO 7 [IDX9054]; SEQ ID NO 6 [IDX9045]; SEQ ID NO 1 [IDX9005]; SEQ ID NO 9 [IDX9074]; SEQ ID NO 3 [IDX9022]; SEQ ID NO 2 [IDX9010]; SEQ ID NO 4 [IDX9030]; and SEQ ID NO 13 [IDX0150].

In an embodiment of the above method, said organ is preferably the heart, and said reduction of the recruitment and/or migration of polymorphonuclear cells to a site of inflammation in said organ is effective to reduce ischemic damage and prevent or alleviate secondary reperfusion injury. In this embodiment, said secondary reperfusion injury may be an injury following from restoring the blood flow to the heart through the administration of a thrombolytic agent. Alternatively, said secondary reperfusion injury is an injury following from restoring the blood flow to the heart through surgical intervention, for example by-pass surgery. Alternatively, said secondary reperfusion injury is an injury following from restoring the blood flow to the heart through balloon angioplasty. Alternatively, said secondary reperfusion injury is an injury following from surgically restoring the blood flow to a transplanted organ in the recipient of the transplant.

In another embodiment of the above method, said organ is the brain, and said ischemic damage is a secondary reperfusion injury. In this embodiment, said secondary reperfusion injury may be an injury following the restoration of the blood flow to the brain through the administration of a thrombolytic agent.

In yet another embodiment of the above method, said organ is chosen among the liver, at least one kidney, the intestines or parts thereof, at least one lung or parts thereof, and said ischemic damage is a secondary reperfusion injury.

In any of the above embodiments of the method, the oligonucleotide is given through one of the following routes of administration: systemic, preferably subcutaneous, intraperitoneal, mucosal, including intestinal, oral, gastric, oesophagal, buccal, nasal, and pulmonary administration.

The inventors also make available an adjuvant method for the treatment of myocardial infarction, wherein an oligonucleotide chosen from the group consisting of: SEQ ID NO 8 [IDX9059]; SEQ ID NO 14 [IDX9052]; SEQ ID NO 7 [IDX9054]; SEQ ID NO 6 [IDX9045]; SEQ ID NO 1 [IDX9005]; SEQ ID NO 9 [IDX9074]; SEQ ID NO 3 [IDX9022]; SEQ ID NO 2 [IDX9010]; SEQ ID NO 4 [IDX9030]; and SEQ ID NO 13 [IDX0150], is administered before, after or simultaneously with the administration of a thrombolytic agent.

Further, the inventors make available an adjuvant method for the treatment of stroke, wherein an oligonucleotide chosen from the group consisting of SEQ ID NO 8 [IDX9059]; SEQ ID NO 14 [IDX9052]; SEQ ID NO 7 [IDX9054]; SEQ ID NO 6 [IDX9045]; SEQ ID NO 1 [IDX9005]; SEQ ID NO 9 [IDX9074]; SEQ ID NO 3 [IDX9022]; SEQ ID NO 2 [IDX9010]; SEQ ID NO 4 [IDX9030]; and SEQ ID NO 13 [IDX0150] is administered before, after or simultaneously with the administration of a thrombolytic agent.

Another embodiment of the invention is a technical solution for the storage and/or transport of transplants, wherein said solution comprises an oligonucleotide capable of influencing the properties and behaviour of polymorphonuclear cells, e.g. suppressing endothelial adhesion and recruitment and/or migration of polymorphonuclear cells, in an amount sufficient for the prevention and/or alleviation of ischemic damage, and said oligonucleotide is chosen among SEQ ID NO 8 [IDX9059]; SEQ ID NO 14 [IDX9052]; SEQ ID NO 7 [IDX9054]; SEQ ID NO 6 [IDX9045]; SEQ ID NO 1 [IDX9005]; SEQ ID NO 9 [IDX9074]; SEQ ID NO 3 [IDX9022]; SEQ ID NO 2 [IDX9010]; SEQ ID NO 4 [IDX9030]; and SEQ ID NO 13 [IDX0150].

In the above methods of use, as well as the methods of treatment, the oligonucleotide is administered in a therapeutically effective dose. The definition of a "therapeutically effective dose" is dependent on the disease and treatment setting, a "therapeutically effective dose" being a dose which alone or in combination with other treatments results in a measurable improvement of the patient's condition. A skilled person can determine a therapeutically effective dose either empirically, or based on laboratory experiments, performed without undue burden. The treating physician can also determine a suitable dose, based on his/her experience and considering the nature and severity of the disease, as well as the patient's condition.

According to one embodiment, the oligonucleotide is given in a dose in the interval of about 1 to about 2000 µg/kg bodyweight, preferably about 5 to about 1000 µg/kg bodyweight, most preferably in a dose in the interval of about 10 to about 500 µg/kg bodyweight.

The oligonucleotide may be administered in a single dose or in repeated doses. The currently most preferred embodiment entails one single dose of the oligonucleotide according to the invention, administered to a mucous membrane, e.g. given intranasally, orally, rectally or intravaginally in an amount of less than about 2000 µg, preferably less than about 500 µg, preferably about 100 µg per kg bodyweight.

Another currently preferred embodiment is the administration of the oligonucleotide in two or three doses, separated in time by about 2, about 6, about 12, or about 24 hours.

According to another embodiment of the invention, the oligonucleotide is administered to an organ designated for transplantation, either in situ, before extraction from the donor, in transit before implantation in the recipient, or in vivo, before or at the time of restoring the blood flow. Preferably the oligonucleotide is present in a concentration of about 0.1 to about 2000 µg/l in a solution used for conditioning the transplant before extraction from the donor. Alternatively, or in addition thereto, the oligonucleotide is present in a concentration of 0.1 to about 1000 µg/l in a solution used for transporting the transplant. Alternatively, or in addition thereto, the oligonucleotide is present in a concentration of 0.1 to about 1000 µg/l in a solution used for conditioning the transplant before restoring blood flow.

There are indications that the oligonucleotide can be administered not only before, but also simultaneously with, or even after restoration of the blood flow. In the context of Example 4, the possibility of pre-conditioning, as well as post-conditioning is discussed. The results surprisingly show that treatment with the SEQ ID NO 8 [IDX9059] also after induction of the stroke can serve as post-conditioning and protect the brain against ischemic injury.

The above embodiments are mutually inclusive, meaning that different doses, modes of administration and time intervals may be freely combined within the embodiments listed, as well as with other embodiments which become apparent to a skilled person.

The above embodiments offer many advantages in that will be evident to a skilled person upon study of the description and examples. One advantage is that the use of the oligonucleotides offers the possibility to replace or to complement currently used drugs, and reduce adverse effects associated with current drugs and treatments.

EXAMPLES

1. Nasal Administration of Immunomodulatory Oligonucleotide Test Substance in a Murine Model of OVA Induced Airway Inflammation Materials and Methods Animals Female Balb/c mice (8 weeks), obtained from B&K Sollentuna, Stockholm, Sweden, were used in the experiment. The mice were fed with a complete pellet rodent diet, R36 (Laktamin A B, Stockholm, Sweden) and water of domestic drinking quality ad libitum. The animals were kept in animal rooms at 21° C., ±3° C., and with a relative humidity of 55%±15%. The ventilation system was designed to give 10 air changes per hour. The room was illuminated to give a cycle of 12 hours light and 12 hours darkness. Light is on from 07:00 h to 19:00 h. The mice were kept in transparent polycarbonate (Macrolone type III) cages (floor area: 820 $cm^2$), 5 in each cage. The bedding in the cages was 4HV Aspen bedding (Tapvei, Finland). Each cage was identified by a cage card marked with study number, group number, sex and animal numbers.

Sensitisation and Aerosol Challenge

Mice were sensitized intraperitoneally with 200 µL OVA/aluminium hydroxide gel (1:3) on day 0 and 12 (FIG. 1a). OVA (chicken egg albumin grade V, Sigma, St. Louis, Mo.) was dissolved in saline and mixed with aluminium hydroxide gel to a concentration of 50 µg/mL by rotation at 4° C. for 3 h. On days 23, 26, 30 and 33 (see FIG. 1a), mice were challenged in the lungs by inhalation of aerosolized OVA for 30 minutes using a Batelle exposure chamber. Aerosols were generated by a compressed-air neubulizer (Collison 6-jet) at airflow 7.4 L/min using a nebulizer concentration of 10 mg/mL OVA dissolved in PBS (Sigma, St Louis, Mo., USA). The control group with non-sensitized animals received no other treatment than aerosolized OVA at day 23, 26, 30 and 33. There was also a control group of sensitized mice which did not receive aerosol challenge.

Oligonucleotide

In this OVA model (FIG. 1a) a selected oligonucleotide, IDX9059, (SEQ ID NO 8, Table 1) was tested. The oligonucleotides were synthesized by biomers.net GmbH, Ulm, Germany and stored frozen at −20° C.

Formulation

The immunomodulatory oligonucleotide was dissolved in phosphate buffered saline (PBS, Fluka Biochemika Ultra, Sigma Aldrich, St. Louis, USA).

Treatment of OVA Induced Airway Inflammation

In this experiment, intranasal instillation of IDX9059 (1,247 µg/µL) on day 16 and 21 in a prophylactic setting (FIG. 1a) was given. The substance was administered in 40 µL PBS giving a dose of ~50 µg/mice (49.88 µg/mice). The two sensitized sham-treatment groups were instilled with PBS, the same total volume as for the test compound on day 16 and 21.

Analysis of Airway Inflammation Parameters

Mice were killed by cervical dislocation 42 h after the last OVA aerosol challenge. The trachea was cannulated with polyethylene tubing (Becton Dickinson, Sparks, Md., USA) and bronchoalveolar lavage (BAL) was performed using 4×1 mL aliquots of ice-cold Hank's balanced salt solution (HBSS) (Sigma, St Louis, Mo., USA). The BAL fluid was centrifuged (400 g, 10 min, 4° C.) and the supernatant recovered and frozen for later analyses. The cells were resuspended in 0.4 mL PBS and the total number of leukocytes counted using trypan blue exclusion in a Bürker chamber. Duplicate Cytospin (Cytospin 3, Shandon, Runcorn, UK) preparations of BAL fluid cells were stained with May Grünewald Giemsa stain for differential counts, using standard morphological criteria.

Statistical Analysis

Statistical comparisons were performed using One-way analysis of variance (ANOVA) using Dunnett's post hoc correction to compare with sensitized PBS treated control mice (GraphPad Prism 4). Data are shown as mean±standard deviation. A P-value below 0.05 was considered significant.

Results

The ovalbumin induced allergic asthma model is a widely used model to reproduce the airway eosinophilia, pulmonary inflammation and elevated IgE levels found during asthma. Analysis of this model relies on general indicators of asthma such as BAL analysis where the type and amount of infiltrating inflammatory cells are identified and counted respectively.

Consequently, the BAL fluid cells derived from each mouse were counted as described and the values plotted as a combined histogram providing mean values for the different groups (FIG. 1b).

In general terms, the level of induced airway inflammation was high as indicated by a large influx of the 4 analyzed cell types into the lungs of the animals (group PBS). The control groups demonstrated no signs of induced inflammation confirming that the animals did not exhibit a natural allergic response to the aerosol ovalbumin protein and that the ovalbumin protein used was not contaminated with, for example, LPS.

The complete absence of any signs of inflammation in the "no aerosol" control groups confirmed that the experimental procedure of OVA immunization itself does not induced lung inflammation.

Following nasal treatment the test substance SEQ ID NO 8 [IDX9059] had a reducing effect on inflammatory cells, i.e. leukocytes (P<0.001), eosinophils (P<0.001) and lymphocytes (P<0.05).

In this in vivo model of allergic asthma leukocyte i.e. PMN mainly eosinophil play an important role in lung inflammation. A statistically significant reduction in the number of leukocytes, eosinophils and lymphocytes infiltrating the BAL fluid was observed in animals when treated with the inventive compound SEQ ID NO 8 [IDX9059]. This indicates that the inventive compound is able to prevent inflammation through inhibition of PMN infiltration.

2. Thioglycolate Induced Pleurisy in C57/Bl6 Mice

Materials and Methods

An animal model was set up to study the effect of oligonucleotides according to an embodiment of the present invention on cell migration and vascular permeability.

Mice were anesthetized by an intraperitoneal injection of 0.15-0.20 ml of a mixture of ketamine (Ketalar® Parke-Davis; 25 mg/ml) and xylazine (Narcoxyl Vet.® Veterinaria AG; 5 mg/ml).

The left jugular vein was cannulated with polyethylene tubing (PE10) for intravenous administration (i.v.). A skin incision was made on the right side of the chest. Following dissection of the underlying muscle, pleurisy (inflammation of the lung sack) was induced by a single intrapleural injection of 100 µl of thioglycolate (Sigma). Sterile PBS was used as negative control. FITC-conjugated dextran in PBS (100 µl, 30 mg/ml) was injected i.v. After 4 h, the animals were euthanized with an overdose of anaesthesia, the chest was carefully opened and the exudate was removed by aspiration and the volume noted. The thorax was then rinsed with 1 ml of ice-cold 3 mM EDTA in PBS. Exudate which was contaminated with red blood cells was discarded.

The exudate and rinse material was centrifuged at 1500 g for 5 min and the supernatant was used for measurement of fluorescence intensity in a fluorometer (Fluoroskan Acsent, LabSystems) and clearance volume of FITC-dextran was calculated. The pellet was resuspended in PBS with 0.1% BSA for 15 min to block unspecific antibody binding. 10 µl of cell suspension was used for differential WBC count in a Bürker chamber.

Cells from the exudate were stained with neutrophil and macrophage specific antibodies and were analyzed by flow cytometry (FACSort and CellQuest software, BD). Analysis included total white blood cell count, based on their typical appearances in the forward and side scatter. PMN and macrophages were further identified by their expression of Ly6G and F4/80, respectively.

In order to test the anti inflammatory effect of oligonucleotides by reducing PMN migration according to embodiments of the present invention, the compounds to be tested were administered intraperitoneally, at a dose of 100 µl, i.e 50 µg/mouse, about 20 minutes before induction of pleurisy. In this study, IDX9010, IDX9054, IDX9059, (SEQ ID NO 2, 7, and 8, respectively, Table 1) and IDX 0150 (SEQ ID NO 13) were tested.

Results

The thioglycolate induced pleurisy model is one of the models of choice for practical screening of new drugs under development although it is technically complicated and can show occasional individual disparate values. However, this model is restricted in the number of animals that can be tested simultaneously.

Results showed that animals responded to the inflammation inducing agent, thioglycolate, by a high immigration of PMN into the pleural cavity, and the accumulation of pleural edema.

Mice (n=4) receiving IDX9010 showed a reduced number of PMN's by 68.2% (FIG. 2a), but no reduction in edema (data not shown). Mice given IDX9054 (n=4) showed no reduction in numbers of PMN, but could reduce the edema by 36% (data not shown). IDX9059 showed reduction in both PMN accumulation (25.1%, FIG. 2b), and edema (31%) (data not shown) in a group of 7 animals. Mice (n=5) given IDX0150 showed 40.9% reduction in PMN-numbers, and 68.2% reduction in edema (data not shown). The results represent mean±SD.

Experiments using an anti-PMN antibody showed that the anti-PMN-ab could equally reduce PMN and edema to the similar levels as the inventive compounds (data not shown). The prophylactic administration of inventive compounds in thioglycolate induced pleurisy led to reduction of PMN migration into the pleural cavity.

3. Intravital Microscopy in a Murine Model of Vascular Inflammation

The in vivo, anti-inflammatory effect of oligonucleotide IDX9059 (SEQ ID NO 8, Table 1) on leukocyte extravasation in mice was investigated. In response to a chemotactic stimulus, inflammatory cells transmigrate the walls of blood vessels towards a gradient of stimulus. To transmigrate, the cells first must intermittently adhere to the vessel inner walls, i.e. rolling (R), thereafter start to adhere more firmly, adherence (A), and then migrate out in the surrounding tissue, transmigration (T). Platelet activation factor (PAF) was used to induce this inflammatory process. In normal unstimulated vessels the order of these events were R>A>T. After exposure to PAF this order was reversed, T>A>R, showing that cells started to adhere and transmigrate.

Introduction

Leukocyte mobilisation is a prerequisite for an inflammatory response. In blood vessels a series of events between white blood cells and endothelium lead to accumulation of inflammatory cells at a site of injury or inflammation (Lindbom, 1983). One important cell in this cascade of events is the polymorphonuclear cell (PMN). PMN's are transported in the blood stream. The blood stream has a higher velocity in the center of the blood vessel and a lower speed towards the margin which allows for contact between the PMN and blood vessel wall. Molecular mechanisms facilitates adherence of PMN's to the endothelium (Penberthy et al., 1997). One group of such molecules are termed selectins. At first this interaction is only partial causing the PMN's to roll along the endothelium. Stimulated by pro-inflammatory molecules, this adherence becomes more firm causing the PMN's to adhere to the endothelium, a phenomenon termed sticking. Sticking allows the PMN's to actively transmigrate the endothelial layer and subsequently enter the connective tissue and are further directed by a gradient of inflammatory factors towards the epicenter of inflammation.

All these events can be studied in vivo by intravital microscopy. Intravital microcopy allows for the study of cells in small vessel, and in the surrounding connective tissue.

Suitable venules have been studied for example in the tenuissimus muscle in rabbits, and in the cremaster muscle of mice.

This example deals with intravital microscopy in the cremaster muscle of mice. The cremaster muscle is the muscle that controls the temperature of the testis in the scrotum. The vasculature of this muscle can readily be exposed under a water immersion objective, super fused with buffered saline at body temperature. Chemotactic or pro-inflammatory substances can be added to the superfusing buffer and pharmacological can be added to the superfusate or into the animal.

Rolling, sticking and transmigration can thereafter be studied by aid of time-lapse video recording and recordings can later be used for quantification of cells or measurements of distances transversed.

The aim of this study was to study effects of the inventive compound IDX9059 on inflammatory cell migration in venules after PAF stimulation in the mouse.

Materials and Methods

Animal material and conditions: C57BL/6 SPF mice from Scanbur AB, Sollentuna, Sweden, were kept in an animal room with controlled temperature (21±2° C.), light-dark cycles of 12 h each, and were allowed free access to food and water.

Test compound: The oligonucleotide DEQ ID NO 8 [IDX9059] was synthesized by biomers.net GmbH, Ulm, Germany under non-GMP conditions and provided in PBS solution. The oligonucleotide was stored at −20° C. as stock solutions and prepared 2-3 days prior to the initiation of the experiment.

Formulation: The oligonucleotide was further diluted in PBS (Fluka, Sigma) at room temperature. The concentration was adjusted by aid of UV spectrophotometry (SmartSpec™ 3000, BIO-RAD, Hercules, USA) to 95% accuracy, until the desired concentration was reached.

Treatment of PAF induced inflammation: The animals were given IDX9059 s.c., 50 µg/100 µl/mouse, circa 20 minutes before induction of inflammation.

Intravital microscopy of leukocyte recruitment: Groups of 4 mice were used. Mice were anesthetized by an intraperitoneal injection of 0.15-0.20 ml of a mixture of ketamine (Ketalar®; Pfizer AB, Sollentuna, Sweden; 25 mg/ml) and xylazine (Narcoxyl Vet.®; Intervet International B.V., Netherlands; 5 mg/ml). The left jugular vein was cannulated with polyethylene tubing (PE10) for continuous administration of anesthesia. A ventral incision was made on the right scrotum and one testis withdrawn. The cremaster muscle was dissected free of fascia, incised, and pinned out flat on a transparent pedestal to allow trans-illumination. The testis was then pinned to the side. The preparation was kept moist and warm by continuous superfusion of a 37° C. temperature controlled bicarbonate buffer, maintaining physiological levels of temperature, pH, and gas tensions. Leukocyte extravasation was induced by addition of platelet activating factor (PAF, Sigma-Aldrich, St. Louis, Mo., USA; 100 nM) to the superfusion solution for 60 min. Measurements of rolling, adhesion and transmigration were made before and after stimulation. Video recordings were obtained from 20-50 µm wide well defined venules. Rolling was determined as the number of leukocytes passing a reference line perpendicular to blood flow during 30 seconds. Cells within the vessel were classified as adherent if they remained stationary for more than 30 seconds. Transmigrated cells were counted in the extra vascular tissue within a distance of 70 µm from the studied vessel.

All microscopic observations were made using a Leitz Orthoplan intravital microscope with a Leitz SW25 water immersion objective (Leitz Wetslar GMBH, Germany). Images were televised and recorded using a Panasonic WV-1550/G (Panasonic, Japan) video camera.

Results

To transmigrate, the cells start rolling, thereafter start to adhere more firmly, and then migrate out in the surrounding tissue. Platelet activation factor (PAF) was used to induce this inflammatory process and in normal unstimulated vessels the order of these events were R>A>T. In the absence of chemoatractant (PAF) SEQ ID NO 8 [IDX9059] were able to reduce rolling by 81.4% and adherence by 41.9% (FIG. 3a).

After exposure to PAF the order of events (rolling, adhesion, and transmigration) was reversed, T>A>R, showing that cells started to adhere and transmigrate. In agreement with that the result shows that when PAF was added, transmigrating cells from a basal level of 1.7 cells/field (before adding PAF, FIG. 3a), reached to 20.66 (after adding PAF, FIG. 3b). there was a reduction of rolling cells from 22.3 cells/field (before adding PAF, FIG. 3a) to 7.7 (after adding PAF, FIG. 3b), and adhering cells stayed at about 14 cells/field. In this condition SEQ ID NO 8 [IDX9059] reduced the rolling, adherence and transmigration after PAF exposure. The reduction was for rolling cells 48.4%, adherent cells by 28.5% and transmigrating cell by 54.4%, showing that SEQ ID NO 8 has anti-inflammatory properties which could be effective on different levels of inflammation and acting on different inflammatory mediators.

Taken together, these results demonstrate the anti-inflammatory effects of SEQ ID NO 8 [IDX9059]. Surprisingly, SEQ ID NO 8 showed lowering effects on rolling and adherence values in the absence of chemotactic agent. This is one indication that this sequence has potential to be used in clinical situations where inhibition of PMN infiltration is preferred.

4. Study of the Inhibitory Effect of Immunomodulatory Oligonucleotides on Cerebral Ischemic Damage in an Experimental Rat Model The objective of the study was to investigate the inhibitory effect on ischemic brain damage by immunomodulatory oligonucleotides in an experimental rat model of cerebral ischemia. The animal study was conducted at the Facility for Division of Experimental Vascular Research, Department of Clinical Sciences, Lund University, Lund, Sweden.

Introduction

It has been shown that, tolerance against ischemic injury can be induced by LPS via TLR4 in various organs such as heart, brain, and kidney (Heemann et al 2000, Rowland et al, 1997; Tasaki et al, 1997). Although the mechanism of protection is not well understood, the paradigm is that a small inflammatory response by LPS-preconditioning mitigates the subsequent damaging of inflammatory response associated with a more powerful secondary stimuli. There are both similarities and differences among the known TLR signalling pathways and both TLR4 and TLR9 are expressed by some cells of immune system and central nervous system (McKimmie and Fazakerley 2005; Tang et al, 2007). Accordingly, CpG oligodeoxynucleotides are believed to trigger activation of the TLR9 within selected cell populations to promote innate immunity and induce Th1 biased adaptive immunity.

One aim of this study was to investigate whether the specific compounds identified by the present inventors also could decrease ischemic injury in the brain similar to LPS-induced tolerance to ischemic brain injury.

Materials and Methods

Animal material and conditions: The rats used were inbred Wistar Hannover rats obtained from Harlan Horst, the Netherlands. The weight of each rat was approximately 350-400 grams. The rats were maintained in standard open cages of type Macrolon 3. Cages were housed in open racks under continuous air flow behind plastic curtains. Standard bedding was purchased from Scanbur-BK, Sollentuna, Sweden. Bedding was changed once a week. The temperature in the animal rooms was 18° C.-22° C. and was controlled via the ambient ventilation system in the laboratory. The light cycle was 12-hour dark and 12-hour light (lights on 06.00).

The rats were given normal rat diet purchased from Scanbur-BK, Sollentuna, Sweden. Water bottles were refilled when necessary during acclimatization and experimentation. Diet and water were administered ad libitum.

The rats had FELASA SPF-status and the housing and changing system was designed to assure that the SPF-status would be preserved during the study. Educated personnel handled the rats. Veterinary expertise was available on short notice from the Veterinary Department at LU. Daily records and decisions made concerning animal welfare.

Test Compounds: IDX9010, IDX9054, IDX9059, and IDX9074 (SEQ ID NO 2, and 7-9, respectively, in Table 1) were tested for their in vivo efficacy of reducing brain damage in an experimental rat model of cerebral ischemia. In addition, a mitogen activated protein kinase inhibitor [1,4-diamino-2,3-dicyano-1,4-bis(2-aminophynyltio)butadiene; $C_{18}H_{16}N_6S_2$] (U0126, Sigma-Aldrich), and PBS (Invitrogen) served as positive and negative controls, respectively. A combination treatment of IDX9059 and U0126 was also used at a later stage in the study. All IDX substances were synthesized by Biomers.net GmbH, Ulm, Germany under non-GMP conditions and provided in PBS solution. The test compounds were stored at −20° C. as stock solutions. With exception of U0126, and the combination therapy (U0126+IDX9059), all other test substances were given in a blinded manner.

Formulation: Prior to the initiation of an experiment the working concentration (1 µg/µl) was prepared by further dilution of the compounds in PBS at room temperature. The concentration was adjusted by aid of UV spectrophotometry (SmartSpec™ 300, Bio-Rad, Hercules, USA) to 95% accuracy.

Animal experiments and dosage: The rats were anesthetized by isofluran (4.5%) mixed with $NO_2$:$O_2$ (70%:30%). Laser Doppler was used to monitor the cortical blood flow of middle cerebral artery (MCA). A filament was introduced into the internal carotid artery, forwarded until it occluded the blood flow in the right MCA; a more than 80% reduction in the Laser Doppler signal (cortical blood flow) confirmed the occlusion.

The blood pressure, blood gases and blood glucose were controlled during the operation. After 90 minutes of occlusion the filament was removed and the circulation of blood continued in the MCA and the cortical blood flow restituted (reperfusion). Only the animals that had more than 80% decrease in blood flow following the occlusion and high recirculation of cortical blood flow were included in the study.

The body temperature and the neurological behaviour (score) were controlled under the operation and at 0, 1, 2, 24, 48 hours after recirculation. A 100 µl of the test compounds together with 200 µl of PBS were injected intraperitoneal to the rats on 0 and 24 hours after recirculation. The animals were sacrificed 48 hours after the end of the operation, and the brain quickly removed and chilled in bicarbonate buffer solution. Two mm thick coronal slices (6 slices) of the brain were prepared and stained with 1% 2,3,5-triphenyltetrazolium chloride (TTC; Sigma Aldrich) dissolved in saline solution. The infarct volume was calculated by numerical integration of the ischemic area of each slice using the trapezium rule and was expressed as percentage of total brain volume in the slices using the software program Brain Damage Calculator 1.1 (MB Teknikkonsult, Lund, Sweden).

Statistics: Statistical analyses were performed using Prism (Graphpad version 4.03, San Diego, Calif., USA). Nonparametric, Mann-Whitney t-test was used to calculate statistical significance. P value of less than 0.05 was considered as statistically significant (*).

Results

The induction of tolerance to ischemic cell death by specific oligonucleotides was investigated in an in vivo model of cerebral ischemia in Wistar Hannover rat.

In total there were 7 different groups in the study. A total of about 60 rats were used in the study with 30% mortality due to the operation. Data were collected throughout the experiments, both in conjunction with the operation and in the follow up period.

Figure 4A:
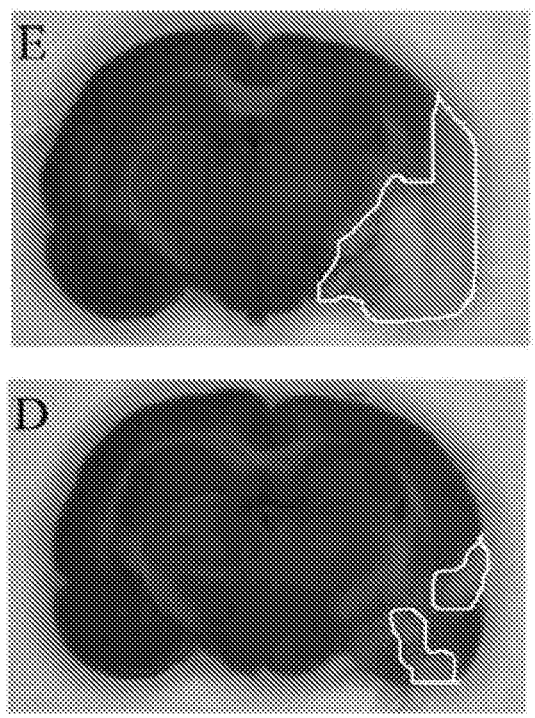
Figure 4B:
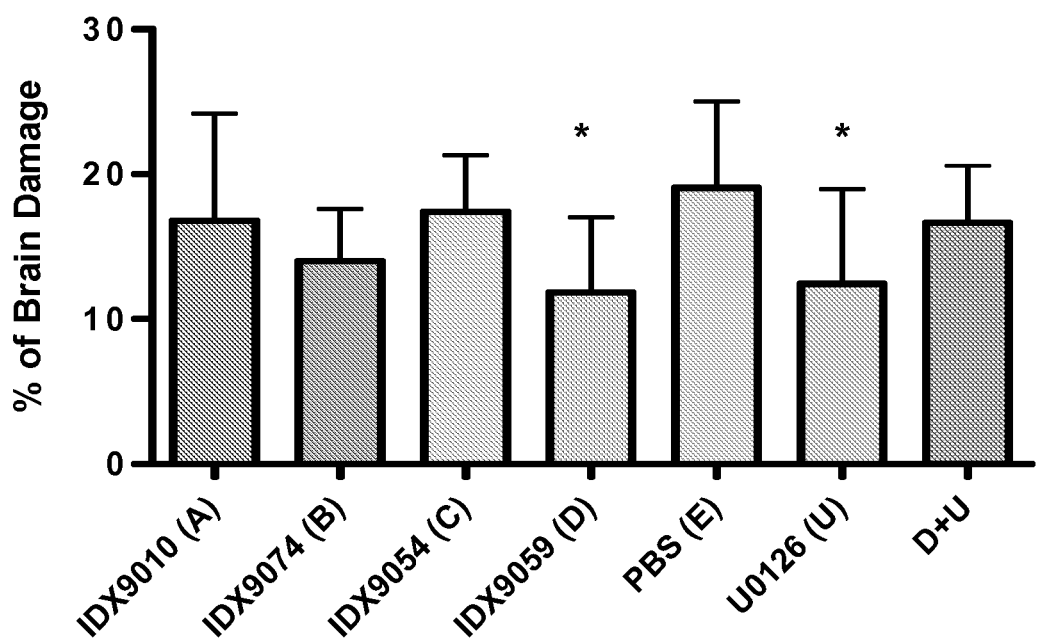
Figure 4C:
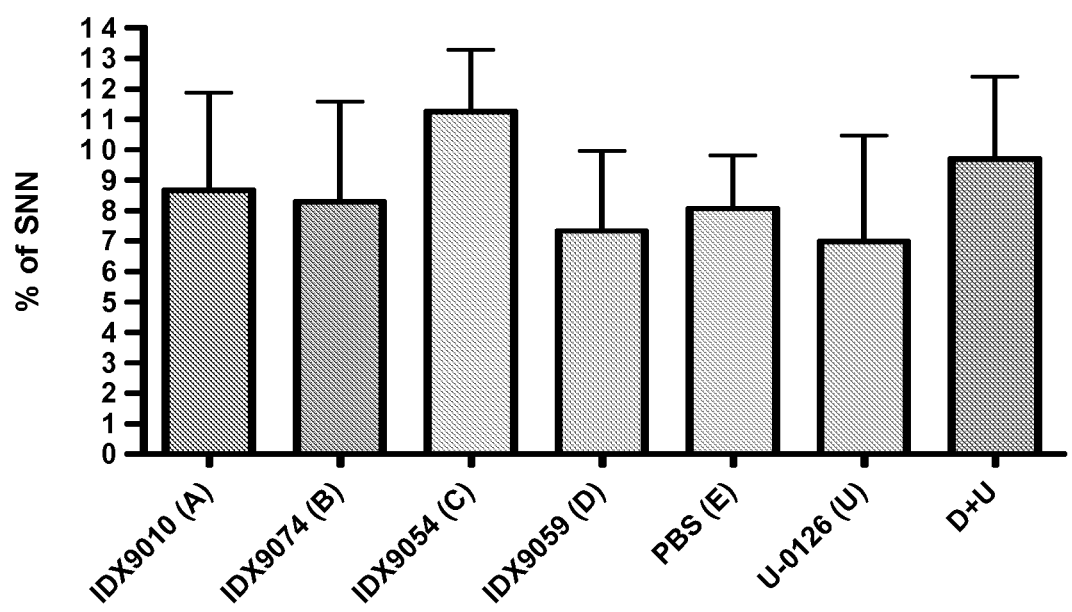
Figure 4D:
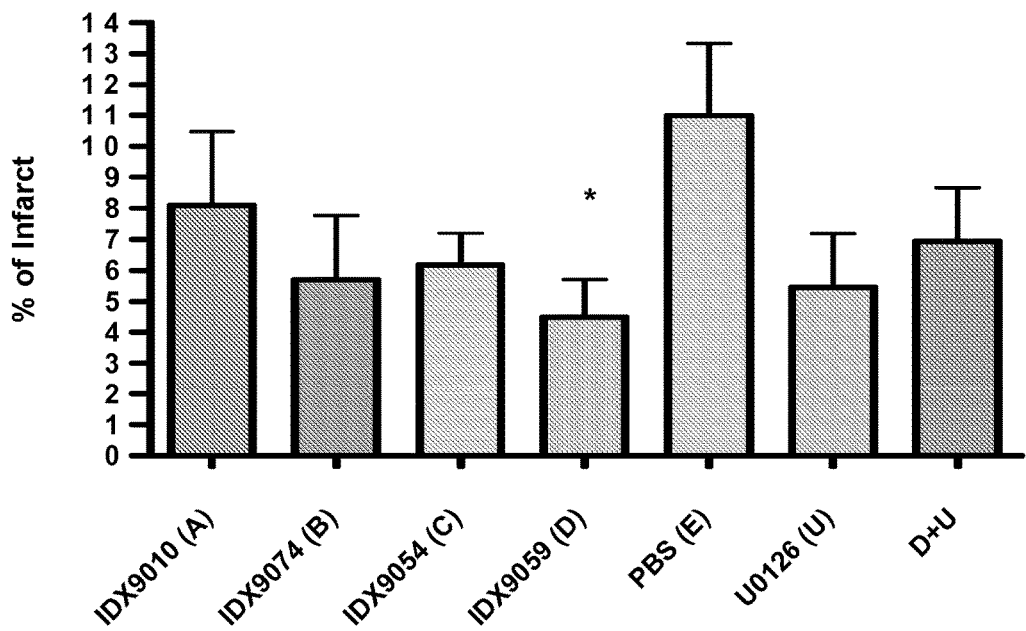

Following TTC staining the intact brain tissue was bright red while regions of damage were pale—white (FIG. 4a). The brains were sectioned and each section was photographed and analyzed with an image program (see Methods). The figures describe various aspects of the cerebral infarct; total infarct area (FIG. 4b), the penumbral area or selective nerve necrosis (SNN) (FIG. 4c), and the ischemic core (the white area as shown in FIG. 4a, interpreted as the core) (FIG. 4d).

The study was performed in a blinded manner for IDX9010 (substance A), IDX9074 (substance B), IDX9054 (substance C), IDX9059 (substance D), and PBS (substance E), but not for U0126 or the combination treatment. As can be seen in FIGS. 4b and 4d, there was marked reduction (35-40%) in infarct volume by substance D (IDX9059) and the control substance U0126. There was no significant difference in reduction of SNN with different substances (FIG. 4c).

After unblinding the study, the last group introduced in the study was the combination of IDX9059 and U0126. The reduction was not as expected additive but less than that seen by each of the substances alone.

The physiological parameters during the experiment and the result of a neurological evaluation were recorded. There was no difference in the physiological parameters between the groups (data not shown). However, the neurology evaluation correlated well with improvements by SEQ ID NO 8 [IDX9059].

The results show that treatment with the SEQ ID NO 8 [IDX9059] after induction of the stroke can serve as postconditioning and protect the brain against ischemic injury.

It has previously been shown that the MEK1/2 inhibitor (U0126) can reduce the infarct size by 30-40% (Henriksson M, 2007, Wang Z Q, 2004). In the present study this substance served as a positive control and when administered i.p., reduced the infarct volume by 33%. There was also a good effect upon the neurology evaluation with improvement by U0126 at 48 hours; thus, confirms that this experiment conducted in accordance with other investigators (Henriksson et al., 2007).

Recently, Stevens et al. (2008) showed that preconditioning with CpG-containing oligonucleotides may induce neuroprotection against ischemic injury and this tolerance is TNF-alpha dependent. Among the 4 inventive compounds (IDX9010, IDX9074, IDX9054, and IDX9059) used in this study, IDX9059 and IDX9074 showed a better neuroprotective effect. However, four oligonucleotides have previously been used in Wistar rats splenocytes studies to evaluate the expression of TNF alpha using quantitative PCR. The results showed that IDX9054, and IDX9010 were able to induce expression of TNF alpha mRNA, whereas IDX9059, and IDX9074 failed to induce TNF alpha. Thus may suggest that there are other factors required, in addition to TNF alpha, that collectively provide neuroprotection. In addition, in the study performed by Steven et al. (2008), the protective effect of CpG-containing oligonucleotides was only seen when it administered prophylactically-14 days before induction of stroke. In the present study, the inventive drugs were given therapeutically 90 min after induction of the stroke, underlining the potency of the SEQ ID NO 8 [IDX9059].

After unblinding of the present study, SEQ ID NO 8 [IDX9059] proved to be most effective at reducing ischemic damage in the brain. As the positive control substance U0126 equally had a pronounced effect at reducing ischemic damage, a combination treatment of U0126 and SEQ ID NO 8 [IDX9059] was also evaluated. The reduction of ischemic injury obtained by the combination treatment was not as expected and the reason for this is unknown. However, it could be that the two substances antagonized each other's effect.

Thus, this in vivo study demonstrated the neuroprotective effect of the inventive compounds in treatment of stroke in a rat model of cerebral ischemia.

5. Study of the Inhibitory Effect of Immunomodulatory Oligonucleotide on Myocardial Ischemic Damage in a Model of Isolated-Perfused Rat Heart The objective of this study was to investigate the possible inhibitory effect of immunomodulatory oligonucleotides on ischemic heart damage in a model of isolated, perfused rat hearts. The animal study was conducted at the animal department, at Ullevål University Hospital, Oslo, Norway.

Introduction

The ability to reduce myocardial infarct size by interrupting myocardial reperfusion with short-lived episodes of coronary re-occlusion has obtained interest in the reperfusion phase as a target for cardioprotection, a phenomenon termed ischemic post-conditioning (I Post). The mechanism of ischemic post-conditioning—induced protection is not fully understood, but the procedure has been shown to target the important mediators of lethal reperfusion injury by reducing oxidative stress, decreasing intracellular Ca2+ overload, improving endothelial function, and attenuating apoptotic cardiomyocyte death (Reviewed in Yelton).

Ischemic preconditioning (IPC) intervention is also used to reduce myocardial infarct size in the experimental setting by subjecting the heart to one or more episodes of non-lethal myocardial ischemia and reperfusion prior to the sustained coronary artery occlusion. Such preconditioning would be beneficial as prophylactic treatment before cardiac bypass surgery (reviewed in Yelton). Both post- and pre-conditioning activates similar group of downstream signaling cascades in RISK pathway (reperfusion injury salvage kinase pathway) that mediate ischemic protection in the heart or brain (Pignataro, 2008). However, both IPC and IPost need an invasive treatment being applied directly to the myocardium in order to achieve cardioprotection, which in some clinical settings can be impractical and harmful.

An alternative more amenable strategy is to apply the cardioprotective stimulus to an organ or tissue remote from the heart, an approach encapsulated by the phenomenon of remote ischemic preconditioning (RIPC). The actual mechanism through which an episode of brief ischemia and reperfusion in an organ or tissue exerts protection against a subsequent sustained insult of ischemia-reperfusion injury in a remote organ or tissue is currently unclear.

The oligodeoxynucleotides trigger activation of Toll-like receptor 9 (TLR9) within selected cell populations to promote innate immunity and induce Th1 biased adaptive immunity. This property of the oligonucleotides modulate inflammation and may provide protection against infectious and non-infectious diseases. Activation of TLR9 by oligonucleotides also targets a series of protein kinases in the RISK pathway (Sun-Hey Lee 2007) similar to IPost and IPC. In previous example (example 4), the inventors showed that oligonucletide IDX9059 is able to reduce ischemia-reperfusion injury in the brain. Therefore one aim of this study was to investigate whether the oligonucleotides which was used to reduce cerebral injury in the previous study also could exert cardioprotective effects during myocardial ischemia-reperfusion.

Materials and Methods

Animal material and conditions: Male Wistar Hannover rats obtained from Scanbur AS, Nittedal, Norway were used in this experiment. The rats were kept in the central animal stable of Ullevål University Hospital. Properly authorized and educated personnel handled the rats. Daily records were made concerning animal welfare. The weight of each rat was approximately 250-350 grams. The rats were randomized into two experimental groups (test and control, n=8 in each group).

The rats were maintained in standard open cages with standard bedding. The temperature in the animal rooms was 18° C.-22° C. and was controlled via the ambient ventilation system in the laboratory (humidity 55-60%). The light cycle was 12-hour dark and 12-hour light (lights on 06.00).

A complete, pellet diet RM3 (Scanbur BK AS, Nittedal, Norway) was supplied ad libitum, and the rats had free access to fresh drinking water bottles.

Test Compounds: The DNA based oligonucleotide IDX9059 (SEQ ID NO 8, Table 1) was synthesized by Biomers.net GmbH, Ulm, Germany (Appendix 1) under non-GMP conditions. The compound was provided in PBS solution and stored at −20° C. as stock solution upon arrival.

Formulation: Prior to the initiation of an experiment the working concentration (1 µg/µl) was prepared by further dilution of the stock solution with PBS (Fluka, Sigma) at room temperature, according to InDex SOPB015. The concentration was adjusted by aid of UV spectrophotometry (SmartSpec™ 300, Bio-Rad, Hercules, USA) to 95% accuracy. The test compound was kept at 4° C. until use.

Animal experiments and dosage: Test drug (1 µg/µl) or placebo (PBS, vehicle of test drug) was given (100 µl) subcutaneously 24 hrs before isolation of the heart. The experiment was performed in a blinded fashion.

Rats were anesthetized by intraperitoneal injection of 5% sodium pentobarbital (60-80 mg kg−1) and heparinised (500 IU i.p). The heart was harvested and perfused for 20 minutes for stabilization at constant pressure of 70 mmHg (modified Langendorff mode at 37° C.) using Krebs Henseleit buffer as perfusate (mmol/L: NaCl 118.5; NaHCO$_3$ 25; KCl 4.7; KH$_2$PO$_4$ 1.2; MgSO$_4$/7H$_2$O 1.2; glucose/1H$_2$O 11.1; CaCl$_2$ 1.8). The buffer was gassed with 95% O$_2$ and 5% CO$_2$ to provide oxygen and maintain at a physiological pH. The heart temperature was kept constant during the experiment by the surrounding glass tube perfused with water from a heating chamber. A fluid-filled latex balloon (Hugo Sachs Elektronik-Harvard Apparatus GmbH, Hugstetten, Germany) was inserted into the left ventricle to measure ventricular pressures by a Powerlab system (AD Instruments Pty Ltd, Castle Hill, NSW 2154, Australia). Left ventricular end-diastolic pressure (LVEDP) was set to 5-10 mmHg, and changes in LVEDP were measured. Left ventricular developed pressure (LVDevP=left ventricular systolic pressure (LVSP)-LVEDP) and maximum and minimum of left ventricular pressure development (LVdp/dtmax and LVdp/dtmin) were calculated. Coronary flow (CF) was measured by timed collections of the coronary effluent. Arrhythmias were counted as an all or nothing response (asystolia or ventricular fibrillation) during the first 30 minutes of reperfusion and evaluated from pressure curves as heart rate (HR). Myocardial temperature was measured by inserting a temperature probe in the right ventricle.

Hearts with LVSP≤100 mmHg, CF≤8 or ≥20 ml min-1, HR≤220 beats per minute before ischemia or irreversible arrhythmias for more than 30 minutes during reperfusion were excluded from the study.

At the end of reperfusion the hearts was cut in four slices of one mm and three slices of two mm (hearts fixed in acrylic rat brain matrix by AgnThor's AB, Lidingö, Sweden). The two mm slices were frozen clamped in liquid nitrogen and stored for possible later analyses (Western blot, real time PCR).

The four ventricular one mm slices (5-8 mm from apex) were incubated at 37° C. in 1% triphenyltetrazoliumchloride (TTC) in PBS for 15 minutes. After incubation the slices were gently pressed between two glass plates and photographed (Nikon, Colorfix5400). The infarct area was measured as percentage of total area and calculated with Adobe Photoshop and ScionImage (Infarct Area Calculation Macro file, Copyright© 1998 Rob Bell, Hatter Institute, UCL, UK).

Extension of necrosis (infarct size) as primary endpoint and heart functions (LVEDP, LVSP, LVDevP, LVdp/dtmax, LVdp/dtmin, HR, arrhytmias, CF) as secondary endpoints were evaluated.

Statistics: For infarct size: Students' t-test, for continuous data analysis of variance repeated measurements.

Results

The induction of tolerance to ischemic cell death by IDX9059 was investigated in an ex vivo model of isolated rat heart. The hearts were excised and perfused in a Longendorff mode and were subjected to an episode of ischemia and reperfusion as described in Material and Methods. Following TTC staining the hearts were sectioned and each section was photographed and analyzed with an image program (see Methods). The infarct injury of the left ventricle showed 35% reduction in the rats treated with IDX9059 compared to rats treated with PBS (vehicle control) (FIG. 5). Various aspects of the heart function during reperfusion were also investigated, however no significant difference in functional data has been observed in IDX9059 treated animals versus control (data not shown).

The results clearly show that subcutaneous pre-treatment of rats with IDX9059 is capable of significantly reducing the extent of global ischemic damage, here by 35%.

The inventors have previously observed that the oligonucleotide IDX9059 reduced the ischemic core in a rat model of cerebral ischemia. In the present study pre-treatment of rats with IDX9059 in a model of isolated/perfused rat hearts was found to increase tolerance and reduce the extent of ischemic injury.

In the isolated heart model many of the factors that may be beneficial are not present, such as the effect via leukocytes. Consequently it is expected that in vivo studies may result in a more pronounced effect.

In the isolated heart the observed protection of IDX9059 may be due to mechanisms initiated in the heart itself. It is reasonable to believe that this is due to molecular changes in the cardiomyocytes via a preconditioning-like stimulation in terms of signalling and effects, following pre-treatment with IDX9059. This could be mediated by different components such as heat shock proteins, nuclear factor kappa B, protein kinases (Hausenloy et al., 2005, and 2007, Valen G 2003, and 2005).

The experiment showed that treatment with IDX9059 reduces PMN migration in different examples above, and indicates that the tested compound also exerts a protective effect through other mechanisms such as preconditioning.

6. Inhibition of Neutrophil Accumulation in Mesenteric Ischemia by Immunomodulatory Oligonucleotides Summary Intestinal ischemia was induced in mice by occlusion of the mesenteric artery. After reperfusion, damage to small and large intestine was evaluated, as well as to the lung.

The anti-inflammatory effect of IDX0150 (SEQ ID NO 13, table 1) was investigated by histology, MPO-assay, tetrasolium reduction and small intestine fluid accumulation.

The study showed that IDX0150 demonstrated significant ameliorating effect compared to control animals given vehicle only when administered 20 minutes before induction of ischemia.

The results indicate that the IDX0150 could be valuable for reduction of reperfusion damage in ischemia.

Materials and Methods

Test Compounds

All compounds were stored at −20° C. as stock solutions and prepared 2-3 days prior to the initiation of an experiment.

Formulation

The oligonucleotides were further diluted in PBS (Fluka Biochemika Ultra, Sigma Aldrich, St. Louis, USA) at room temperature. The concentration was adjusted by aid of UV spectrophotometry (SmartSpec™ 3000, BIO-RAD, Hercules, USA) to 95% accuracy, until the desired concentration was reached (InDex SOP B015).

Animal Experiments

Animal Department

The MTC animal department is monitored and supervised by the Karolinska Institute Veterinary Department. The animal department has set routines to maintain a high quality animal facility. The animal study was carried out in a non-GLP accredited academic research laboratory.

Animals

Female BALB/cJ SPF mice, age 10-30 weeks, (originating from The Jackson Laboratory, Bar Harbor, Me., USA were kept at MTC's CFGR department at Karolinska Institutet, Stockholm). The animals were grouped and allowed to acclimatize for at least one week before the start of an experiment. The animals were kept together with sentinels who were tested according to FELASA regulations (5) at a minimum twice a year.

Housing

The animals were kept in rooms at 21±3° C., and with a relative humidity of 55±15%. The ventilation system has been designed to give 10 air changes per hour. The room was illuminated to give a cycle of 12 hours light and 12 hours darkness. Light was on from 06:00 to 18:00 hours.

The mice were kept in transparent polycarbonate (Macrolone type III, Scanbur AB, Sollentuna, Sweden) cages (floor area: 810 cm$^2$), 8 in each cage.

Bedding

The bedding in the cages was Scanbur Bedding (Scanbur AB, Sollentuna, Sweden).

Environmental Enrichment

For environmental enrichment, the animals were given a supply of Sizzle-nest or Happi-Mat, (Scanbur AB, Sollentuna, Sweden)

Diet and Drinking Water

A complete, pellet rodent diet, R36 (Lantmannen, Kimstad, Sweden) was supplied ad libitum. The animals had free access to animal drinking bottles with domestic quality drinking water.

Animal Identification, Grouping and Treatment

Each cage was identified by a cage card marked with study number, group number, and sex. The animals were individually marked on the tail with transverse lines corresponding to the animals' number, using a permanent-ink felt pen.

Test Procedure

Induction of Ischemia and Reperfusion

The mouse was anesthetized with Isofluran (Forene®, Abbott Scandinavia AB, Solna, Sweden) thereafter kept on surgical anesthesia (Univentor 400 anesthesia unit, AgnTho's AB, Lidingo, Sweden) and placed on a heating pad, controlled by a thermocoupled thermometer (Pharmacia AB, Uppsala, Sweden) controlled by a rectal thermistor maintaining a body temperature of 37° C. With the aid of an operating surgical stereomicroscope (Leitz Wild, Wetslar, Germany) a 4-5 cm long incision was made in the abdomen and the cranial (superior) mesenteric artery was localized. A micro vessel clamp, Biemer-clip, closing force 0.20-0.25 N, Aesculap-Werke AG, Tuttlingen, Germany) was placed over the artery to totally occlude the blood stream indicated by lack of pulsation and paleness. The abdomen was closed and a gauze pad soaked with saline (0.9% (w/v$^{-1}$ NaCl) solution was placed over the abdomen. The blood flow was reinstated after 15 minutes, indicated by return of pulse and redness in the vessel. The abdomen was closed with agraffes or surgical sutures. The mouse was given 2 mL sterile saline s.c. to maintain physiological conditions. Buprenorphin (Temgesic®, Schering-Plough Corp., New Jersey, USA), 0.05 to 0.1 mg/kg was given for analgesia. After 3 hours, the animal was anesthetized, and blood was sampled from the eye orbital plexus. Samples were taken from intestines and liver for histology and other analyses.

Pharmacological Treatment

Subcutaneous (s.c.) injections of 50 µg/100 µL IDX0150, were given in the animal's neck about 20 minutes before induction of ischemia or immediately after starting of reperfusion.

Clinical Signs

Each mouse was observed regularly until killed. All signs of illness, health and any behavioral changes were recorded.

Clinical Parameters

The inflammatory effects were graded using an inflammatory scoring system, intestinal redness: normal 0, little redness 1, red 2, very red 3; intestinal fluid: normal 0, little 1, much 2; animal behavior: alert 0, lethargic 2.

Homogenization of Lung and Intestinal Tissue for MPO Measurement

Lungs and small intestine (100-200 µg) were collected from IDX0150 and PBS-treated mice subjected to intestinal ischemia and reperfusion injury. The tissues were homogenized for 30 seconds on ice using Disperser T 10 (IKA®-Werke GMBH & Co. KG, Staufen, Germany) in 1 ml RIPA buffer (Sigma Aldrich, St. Louis, Mo., USA) containing 5 mM EDTA (Sigma Aldrich) and protease inhibitor cocktail (Sigma Aldrich). The samples were thereafter incubated on ice for 30 min, after which debris was removed from the homogenates by two rounds of centrifugation at 10,000×g for 10 min at 4° C. The supernatants were collected, aliquoted and frozen at −70° C. for later myeloperoxidase (MPO) measurements. MPO were analyzed in the homogenates using a MPO ELISA kit (Hycult biotechnology, Uden, Holland) according to the manufacturer's instructions.

Results

The ischemia induced a profound inflammatory response which was seen as lethargy and pile erection of the fur, upon necropsy the intestines were bloated, containing fluid and were inflamed (FIG. 6a). In the IDX0150 treated animal the intestine was less inflamed (FIG. 6b). Using a scoring system the inflamed animals had a score of 6.5 which was contrasted by a lower score in animals receiving i.p. IDX0150 treatment (FIG. 6c).

Myeloperoxidase (MPO) is a heme protein abundantly expressed in polymorphonuclear neutrophils and is used as a marker of neutrophils infiltration and activation (Lau and Baldus, 2006). Neutrophils are the major leukocytes infiltrating the ischemic tissue and are an important contributor to the induced inflammation.

Figure 6E:
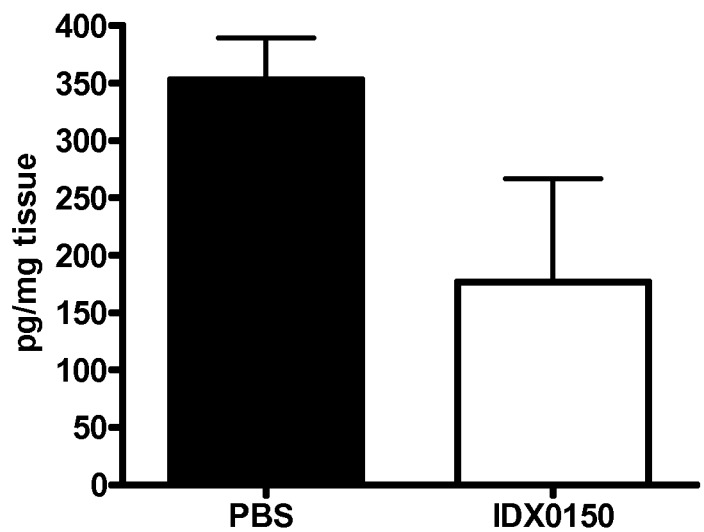
Figure 6F:
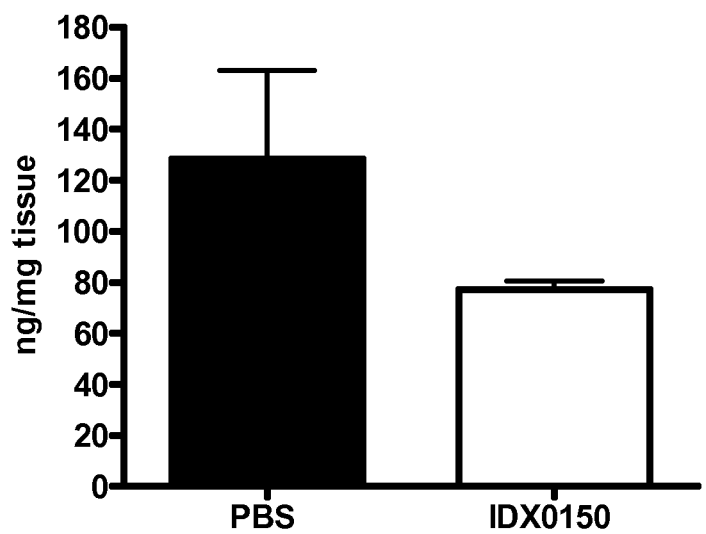
Figure 6G:
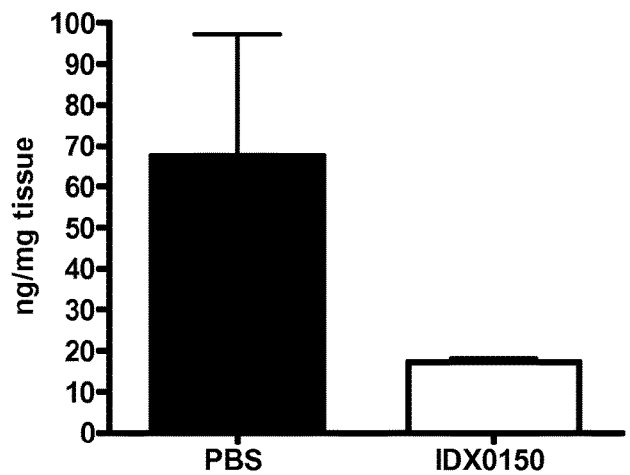

In this study the effect of the oligonucleotide compound IDX0150 (SEQ ID NO 13, Table 1) on the infiltration of neutrophils into small intestine and lung in a mouse model of intestinal ischemia and reperfusion injury was investigated by measuring MPO in homogenized tissue. The MPO levels in both intestinal (FIGS. 6d, and e) and lung (FIGS. 6f, and g) tissue were reduced in mice treated with IDX0150 compared with PBS treated controls. This decrease in MPO was seen if the compound was administered before induction of ischemia (FIGS. 6d, and f) as well as after starting the reperfusion (FIGS. 6e, and g). The observed reduction in MPO indicates that there is a reduced infiltration of neutrophils into the ischemic tissue in response to the oligonucleotide compounds of the invention.

These results were also reflected in the clinical results with a reduction in inflammatory score.

7. The Effect of Immunomodulatory Oligonucleotides on the Expression of Chemokine Receptors on Polymorphonuclear Cells Introduction IL-8 is a potent proinflammatory cytokine that has a key role in the recruitment and activation of neutrophils during inflammation. IL-8 reacts with neutrophils via two distinct types of receptors (CXCR1 and CXCR2). Chemotaxis of neutrophils to IL-8 is mediated predominantly by CXCR1 (78%) and the rest by CXCR2. Another potent chemoattractant for neutrophils is Leukotriene $B_4$ ($LTB_4$), which binds with high affinity to the receptor BLT1 expressed on the surface of neutrophils. The aim of this study was to investigate whether the inventive compounds are able to decrease the expression of CXCR1/2 and BLT1 and thereby reducing the infiltration of PMN.

Materials and Methods

Test Compounds

IDX9005, IDX9010, IDX9022, IDX9030, IDX9031, IDX9045, IDX9052, IDX9054, IDX9059, IDX9074, IDX9092, IDX9095, IDX9096 and IDX0150 (SEQ ID NO 1 to 14, Table 1) were investigated for their effect on CXCR1 and CXCR2 surface expression in healthy polymorphonuclear cells (PMN). The inventive compounds IDX9022, IDX9052, IDX9054 and IDX9059 (SEQ ID NO 3, 14, 7 and 8, Table 1) were further investigated for their effect on BLT1 surface expression in PMN from healthy volunteers. All oligonucleotides were synthesized by Biomers.net (Ulm, Germany), except IDX0150 which was ordered from Avecia (Manchester, United Kingdom).

Formulation

The oligonucleotides were adjusted with phosphate buffered saline (PBS, Invitrogen, Carlsbad, Calif.) to reach a stock concentration of 500 μM by aid of UV spectrophotometry (SmartSpec® 3000, BIO-RAD, Hercules, USA) and stored at −20° C. until used.

Cell Preparation and In Vitro Stimulation with Oligonucleotides

Whole blood from healthy blood donors were used for preparation of PMN. PMN were isolated by density centrifugation using Polymorphprep™ (Axis-Schield, Oslo, Norway). The cells were then further washed in PBS, and the viability and the cell number were determined by counting the cells in Trypan blue (Sigma Aldrich, Stockholm, Sweden). Thereafter, the cells were re-suspended in complete cell medium consisting of RPMI 1640 (Sigma Aldrich) supplemented with 10% heat inactivated fetal calf serum (FCS, Invitrogen), 2 mM L-glutamine, 100 U/mL penicillin, 100 μg/mL streptomycin, 10 mM HEPES (Sigma Aldrich) and 5 μg/mL gentamicin (Invitrogen). The PMN were cultured in 96-well culture tissue plates (Becton Dickinson, Franklin Lakes, N.J.) at a concentration of $2 \times 10^6$ cells/mL with 0.5, 10 μM or 25 μM of the inventive compounds or with medium alone as a negative control in a total volume of 200 μl/well. The cells were incubated for 3 h, if not stated otherwise, at 37° C. in a humidified cell culture incubator (Thermo Scientific, Waltham, Mass.) with 5% $CO_2$, after which the cells were analyzed for CXCR1, CXCR2 and BLT1 expression using flow cytometry as described below.

Kinetic Evaluation of the Effect of Oligonucleotides on CXCR1 Surface Expression Human PMN from healthy blood donor were stimulated with 10 μM of IDX9059 (SEQ ID NO 8, Table 1) or with medium alone for various time points (15 min, 30 min, 1 h, 2 h, and 3 h). Cells were subsequently harvested and fixated at each time point in 2% paraformaldehyde, after which they were analyzed for CXCR1 expression by flow cytometry as described below.

Flow Cytometry

Cells incubated with the inventive compounds were harvested, washed in PBS and resuspended in PBS supplemented with 2% FCS. The cells were stained for the granulocyte marker CD66b together with CXCR1 or CXCR2 or BLT1 using fluorochrome labeled mouse monoclonal antibodies (Becton Dickinson, San Jose, Calif., USA) for 30 min at 4° C. The antibodies used were compared with isotype matched controls (Becton Dickinson). After washing in PBS, the cells were analyzed by a FACSarray flow cytometer (Becton Dickinson) and the data were analyzed using the FACSarray software system (Becton Dickinson). A minimum of 15 000 gated PMN were analyzed per sample.

Chloroquine Assay

PMN isolated from healthy blood donors were pretreated with 0.5, 5 and 10 μg/ml of Chloroquine (Sigma Aldrich) for 30 min at 37° C. before stimulated with 10 μM of test substances for an additional 3 h. Surface expression of CXCR1 and CXCR2 were then analyzed by flow cytometry as described above.

Chemotaxis Assay

Chemotaxis of PMN was investigated using the QCM™ 3 μm 24-well colorimetric chemotaxis assay (Millipore, Temecula, Calif.) according to the manufacturer's instructions. Briefly, PMN were prepared from whole blood from healthy donors and resuspended in complete cell medium as described above. PMN were pre-incubated in 48-well plates (Becton Dickinson) at a concentration of $1 \times 10^6$ cells/mL, using 250 μl cell suspension per well, with 0.5, 10 or 25 μM of the inventive compounds for 1 h at 37° C. in a humidified cell culture incubator (Thermo Scientific) with 5% $CO_2$. The cells were then washed in complete cell medium and the cells were transferred to the top inserts of a 24-well cell migration plate assembly having a pore size of 3 μm (Millipore). To the lower chambers, complete cell medium containing 100 ng/ml of recombinant human IL-8 (Invitrogen) or 500 nM $LTB_4$ (Sigma Aldrich) were added. In one experiment testing IDX9045 the cells were not washed before added to the top inserts of the chemotaxis plate and in this case IL-8 were added together with IDX9045, at the same concentration as used for the top insert, to the lower chamber, this to eliminate the risk of creating a gradient of the compound. The cells were then allowed to migrate through the filter towards the chemoattractant for 3 h at 37° C. in a humidified cell culture incubator (Thermo Scientific) with 5% $CO_2$. Thereafter, the cells from the lower chamber, i.e. migrated cells, were detected by incubation with the cell viability stain WST-1 for 1 h followed by quantification by measuring the absorbance at 450 nm using a microplate reader (Tecan, Mannedorf, Switzerland).

Result and Discussion

PMN are the major leukocytes that are attracted to the ischemic tissue. Here, neutrophils add to the tissue damage by releasing free radicals, proteolytic enzymes such as myeloperoxidase and by stimulating cytokine release from local cells leading to increased inflammation. IL-8, by binding to its receptors CXCR1 and CXCR2, and $LTB_4$, by binding to its receptor BLT1 on the PMN cell surface, play a key role in the recruitment of neutrophils to the inflammation site (Kobayashi, 2008; Tager and Luster, 2003).

In this study the effect of oligonucleotide compounds on the surface expression of CXCR1, CXCR2 and BLT1 on PMN isolated from healthy blood donors were investigated. After 3 h of stimulation with test substances several of the inventive compounds decreased the mean fluorescence intensity (MFI) of CXCR1, i.e. the amount of CXCR1 expressed per cell (FIG. 7a). The largest reduction in CXCR1 expression was induced by IDX9052, IDX9054, IDX9005, IDX9030, IDX9059, IDX9022, and IDX9045 (SEQ ID NO 14, 7, 1, 4, 8, 3, and 6, Table 1), by which the MFI was decreased by 68%, 62%, 61%, 60%, 53%, 52% and 30%, respectively when used at 25 μM. In addition, there was a small decline in the percentage of CXCR1+ cells in PMN stimulated with IDX9005, IDX9022, IDX9030, IDX9052, IDX9054 and IDX9059 (SEQ ID NO 1, 3, 4, 14, 7 and 8, Table 1) however, the reduction was not as substantial as for the MFI (FIG. 7b). CXCR2 was also down-regulated in response to the inventive oligonucleotide compounds (FIG. 7c), especially when PMN were stimulated with IDX9052 and IDX9054 (SEQ ID NO 14 and 7, Table 1), which induced a decrease in the MFI of CXCR2 by 50 and 36%, respectively. IDX9052 and IDX9054 also induced a small decrease in the percentage of CXCR2+ PMN (FIG. 7d). The reduction in CXCR2 expression was dose-dependent with the biggest effect seen at 25 μM of oligonucleotide compound and with less effect seen at 10 and 0.5 μM (FIG. 7e). In addition, in a separate experiment using PMN from healthy blood donors, IDX9074 (SEQ ID NO 9, Table 1) were able to down-regulate the expression of CXCR1 (FIG. 7f).

To investigate the kinetics for CXCR1 down-regulation, human PMN were stimulated with 10 μM of IDX9059 (SEQ ID NO 8, Table 1) for 15 min, 30 min, 1 h, 2 h and 3 h after which CXCR1 expression was investigated with flow cytometry. Already after 15 min, a small decrease of CXCR1 surface expression could be observed and after 2 h the down-regulation had reached maximum level with no further decrease seen after 3 h (FIG. 7g).

The inventive compounds IDX9052, IDX9054, IDX9059, IDX9005 and IDX9045 (SEQ ID NO 14, 7, 8, 1, and 6) were all very efficient in reducing CXCR1/2 expression and have in common that they all contain a G-flank in their 5'- and/or 3'-end, suggesting that this structural motif, together with the sequence of the oligonucleotide, could be associated with a more efficient CXCR1/2 reducing capacity by the oligonucleotides. To further support this, when PMN from healthy blood donors were incubated with the control oligonucleotides IDX0480 (T*G*C*TGCTTCTGCCATGCT G*C*T*T) and IDX9134 (G*A*T*GCTCTG*G*G*G), which have the same sequences as IDX9022 and IDX9059, respectively, but without CpG motifs, IDX0480 was unable to reduce the surface expression of CXCR1 as seen for IDX9022, while IDX9134 was equally potent as IDX9059 in reducing CXCR1 surface expression (FIG. 7h). Without wishing to be bound by any theory, the inventors contemplate that these results indicate that IDX9022, which does not have a G-flank, mediates its CXCR1 and CXCR2 reducing effect mainly through its CpG motifs, while IDX9059 containing a G-flank has CpG-independent effects.

To investigate the role of TLR9 in the reduction of CXCR surface expression induced by the test substances, PMN were pretreated with Chloroquine before stimulated with test substances. Chloroquine is a 4-aminoquinoline drug, which blocks endosomal fusion and acidification and prevents TLR9 activation and downstream metabolic signaling pathways. Chloroquine could dose-dependently inhibit the reduction in CXCR1 surface expression induced by IDX9059 and IDX9022 (SEQ ID NO 8 and 3, Table 1) (FIG. 7i). 10 μg/ml of Chloroquine almost completely blocked the decrease in CXCR1 expression induced by these two compounds (FIG. 7i). However, chloroquine could not block the reduction in CXCR1 surface expression induced by IDX9054 or IDX9052 (SEQ ID NO 7 and 14, Table 1) (FIG. 7i). These results indicate that some of the inventive compounds mediates their CXCR reducing effect through endosomal TLR9 activation (i.e. IDX9022 and IDX9059), while others do not (i.e. IDX9052 and IDX9054).

A dose-dependent reduction of BLT1, the receptor for the chemoattractant $LTB_4$, could also be demonstrated after incubation with different concentrations (0.5. 10 and 25 μM) of the inventive compounds (FIG. 7j). An 87%, 80%, 64% and 57% reduction in the MFI was seen with the inventive compounds IDX9052, IDX9054, IDX9059 and IDX9022 respectively (SEQ ID NO 14, 7, 8 and 3, Table 1) when used at 25 μM (FIG. 7j). In addition, IDX9052 and IDX9054 significantly reduced the percentage of BLT1 positive PMN (FIG. 7k). As shown in FIG. 7j the inventive compounds containing a G-flank in their 5'- and/or 3'-end, i.e. IDX9052, IDX9054 and IDX9059 (SEQ ID NO 14, 7 and 8, Table 1) were more efficient in reducing BLT1 surface expression, compared to IDX9022 which does not have a G-flank.

To investigate if the reduction in CXCR1, CXCR2 and BLT1 surface expression induced by the inventive compounds also leads to decreased migration of PMN towards the CXCR1 and CXCR2 ligand (IL-8) or the BLT1 ligand (LTB$_4$), PMN from healthy blood donors were pre-incubated for 1 h with the inventive oligonucleotide compounds. The cells were then allowed to migrate towards IL-8 or LTB$_4$ in a chemotaxis assay for 3 h. A dose dependent reduction in the number of migrated PMN were seen after pre-incubation with both IDX9022, IDX9052, IDX9054 and IDX9059 (SEQ ID NO 3, 14, 7 and 8, Table 1), with the most efficient compounds being IDX9052, IDX9054 and IDX9059, which at 25 µM completely or almost completely blocked the migration of PMN towards both IL-8 (FIG. 7*l*) and LTB$_4$ (FIG. 7*n*). In addition, In a separate experiment using PMN from two healthy blood donors, IDX9045 (SEQ ID NO 6, Table 1) dose-dependently reduced IL-8 induced migration of PMN (FIG. 7*m*).

The surface expression of CXCR1 and 2 correlated with the number of migrated PMN in the IL-8 induced chemotaxis, as did the surface expression of BLT1 and the number of migrated PMN in the LTB$_4$ induced chemotaxis (FIG. 7*o-q*). This indicates that the reduction in PMN migration is due to a lower surface expression of the receptors.

The inventors demonstrated a rapid reduction in CXCR1, CXCR2 and BLT1 expression on PMN incubated with oligonucleotide compounds, that for CXCR1 was shown to start already after 15 min of stimulation. This is very important since neutrophils are terminally differentiated cells and therefore short lived, why a quickly induced immunomodulatory effect are desired. Hayashi et al, in 2003, demonstrated a down-regulation of CXCR1 expression on PMN by CpG DNA only in cells pretreated with GM-CSF (Hayashi et al., 2003), whereas in this study, the inventive oligonucleotide substances reduced surface expression of CXCR1 and 2 without cytokine pretreatment, underlining their potent immunomodulatory properties.

The inventors not only demonstrate a reduction in the surface expression of CXCR1, 2 and BLT1 but in addition demonstrate a reduced responsiveness of the cells to the chemoattractants IL-8 and LTB$_4$ resulting in less migration. There is reason to predict that these results also reflect an in vivo scenario, consequently leading to less chemotaxis of PMN into inflamed tissues.

A decreased surface expression of CXCR1, CXCR2 and BLT1 as well as reduced responsiveness of the cells to the chemoattractants IL-8 and LTB$_4$ was observed in healthy PMN treated with the inventive compounds. These properties of the oligonucleotide compounds clearly show the potency of the inventive compounds to influence the properties and behavior of PMNs.

8. The Effect of Immunomodulatory Oligonucleotides on the Expression of Chemokine Receptors on Polymorphonuclear Cells from Asthmatic and MS Patients Introduction PMN is involved in the pathogenesis of not only ischemia, but also of many other inflammatory disorders, and blocking PMN functions would therefore be beneficial in many inflammatory diseases. Cellular inflammation of the airways with PMN, i.e. eosinophils and neutrophils, is a characteristic feature of asthma. PMN has also been described to be involved in the pathogenesis of Multiple Sclerosis (MS). The aim of this study was to investigate whether the inventive compounds are able to decrease the expression of CXCR1/2 and BLT1 not only in PMN from healthy individuals, but also in PMN from patients with an inflammatory condition, in this case exemplified by asthma and MS.

Materials and Methods

Test Compounds

IDX9022, IDX9052, IDX9054 and IDX9059 (SEQ ID NO 3, 14, 7 and 8, Table 1) were investigated for their effect on CXCR1, CXCR2 and BLT1 surface expression in PMN from asthmatic and MS patients. All oligonucleotides were synthesized by Biomers.net (Ulm, Germany).

Formulation

The oligonucleotides were adjusted with phosphate buffered saline (PBS, Invitrogen, Carlsbad, Calif.) to reach a stock concentration of 500 µM by aid of UV spectrophotometry (SmartSpec® 3000, BIO-RAD, Hercules, USA) and stored at −20° C. until used.

Cell Preparation and In Vitro Stimulation with Oligonucleotides

Whole blood from asthmatic and MS patients were used for preparation of PMN. PMN were isolated, counted and resuspended in complete cell medium as described in materials and methods under example 7. The PMN were cultured in 96-well culture tissue plates (Becton Dickinson, Franklin Lakes, N.J.) at a concentration of 2×10$^6$ cells/mL with 0.5, 10 µM or 25 µM of oligonucleotides or with medium alone as a negative control in a total volume of 200 µl/well. The cells were incubated for 3 h at 37° C. in a humidified cell culture incubator (Thermo Scientific, Waltham, Mass.) with 5% CO$_2$, after which the cells were analyzed for CXCR1, CXCR2 and BLT1 expression using flow cytometry.

Flow Cytometry

Cells incubated with oligonucleotides were harvested, washed in PBS and resuspended in PBS supplemented with 2% FCS. The cells were stained for the granulocyte marker CD66b together with CXCR1 or CXCR2 or BLT1 as described in materials and methods under example 7. The cells were then analyzed by a FACSarray flow cytometer (Becton Dickinson) and the data were analyzed using the FACSarray software system (Becton Dickinson). A minimum of 15 000 gated PMN were analyzed per sample.

Result and Discussion

PMN are one of the major cells mediating tissue damage during an inflammatory response. PMN migrate from the blood to sites of inflammation in response to locally produced chemoattractants. Two of the major mediators of PMN migration are the CXC chemokine IL-8 and the leukotriene LTB$_4$. In this study, the inventors set out to investigate if the inventive compounds could down-regulate the receptors for IL-8, i.e. CXCR1 and CXCR2, as well as the receptor for LTB$_4$, i.e. BLT1, on the surface of PMN derived from patients with an inflammatory disease.

Using blood from MS patients indicated a dose-dependent reduction of CXCR1, CXCR2 and BLT1 on PMN after stimulations with the inventive compounds. (FIG. 8*a-f*). Similar results were seen when blood from an asthmatic patient was used (FIG. 8*g-i*). The reduction was predominantly seen for the MFI, i.e. the amount of receptors expressed per cell. IDX9052, IDX9054 and IDX9059 (SEQ ID NO 8, 7 and 14, Table 1) induced a reduction of the MFI for CXCR1 on PMN from MS patients with 45%, 56% and 42% respectively when used at 25 µM (FIG. 8*a*). In addition, IDX9052, IDX9054 and IDX9059 reduced the surface expression of CXCR2 with 76%, 58% and 39% (FIG. 8*c*), and the surface expression of BLT1 with 50%, 47% and 26%, respectively (FIG. 8*e*). When stimulating PMN from an asthmatic patient with the inventive compounds, the reduction in MFI for CXCR1 was 56%, 71% and 62% with IDX9052, IDX9054 and IDX9059 (FIG. 8*g*), respectively. IDX9052, IDX9054 and IDX9059 also reduced the MFI for CXCR2 on PMN from an asthmatic patient with 69%, 50% and 37% (FIG. 8*h*), and the MFI for BLT1 with 85%, 77% and 64% (FIG. 8*i*), respectively. As seen with PMN from healthy donors, the inventive compounds containing a flanking oligo-G sequence, i.e. IDX9052, IDX9054 and IDX9059 (SEQ ID NO 14, 7 and 8, Table 1) were the most efficient in reducing CXCR1, CXCR2 and BLT1 surface expression also in PMN derived from MS and asthma patients.

A decreased surface expression of CXCR1, CXCR2 and BLT1 was also observed when PMN derived from patients with an inflammatory disorder, i.e. asthmatic and MS patients, were treated with the inventive compounds. These properties of the oligonucleotide compounds could be useful in reducing the infiltration of PMN into inflamed tissues.

Although the invention has been described with regard to its preferred embodiments, which constitute the best mode presently known to the inventors, it should be understood that various changes and modifications as would be obvious to one having the ordinary skill in this art may be made without departing from the scope of the invention as set forth in the claims appended hereto.

REFERENCES

Cooper, et al., Transendothelial migration of neutrophils involves integrin-associated protein (CD47), Proc Natl Acad Sci USA, 1995 Apr. 25, 92(9): 3978-82

Entman M L, Smith C W. Postreperfusion inflammation: a model for reaction to injury in cardiovascular disease. Cardiovasc Res. 1994; 28(9):1301-11. Review.

Hausenloy, D. J., A. Tsang and D. M. Yelton. The Reperfusion Injury Salvage Kinase Pathway: A Common Target for Both Ischemic Preconditioning and Postconditioning. Trends Card Med. 2005; 15: 69-75.

Hausenloy D J, Yelton D M. Preconditioning and postconditioning: united at reperfusion. Pharmacol Ther 2007; 116:173-91.

Hayashi F, Means T K, and Luster A D. Toll-like receptors stimulate human neutrophil function. Blood. 2003; 102: 2660-2669.

Heemann U, Szabo A, Hamar P, Müller V, Witzke O, Lutz J, Philipp T. Lipopolysaccharide pretreatment protects from renal ischemia/reperfusion injury: possible connection to an interleukin-6-dependent pathway. Am J Pathol. 2000; 156:287-93.

Henriksson M, Stenman E, Vikman P, Edvinsson L. MEK1/2 inhibition attenuates vascular ETA and ETB receptor alterations after cerebral ischaemia. Exp Brain Res. 2007: 178(4):470-6.

Kobayashi, Y. The role of chemokines in neutrophil biology. Front Biosci, 2008 Jan. 1; 13, 2400-2407.

Lee S H, Lee J G, Kim J R, Baek S H. Toll-like receptor 9-mediated cytosolic phospholipase A2 activation regulates expression of inducible nitric oxide synthase. Biochem Biophys Res Commun. 2007; 28; 364(4):996-1001.

Lindberg et al., Decreased resistance to bacterial infection and granulocyte defects in IAP-deficient mice, Science, 1996 Nov. 1; 274(5288): 795-8

Lindbom L. Microvascular blood flow distribution in skeletal muscle. An intravital microscopic study in the rabbit. Acta Physiol Scand Suppl. 1983; 525:1-40.

McKimmie C S, Fazakerley J K. In response to pathogens, glial cells dynamically and differentially regulate Toll-like receptor gene expression. J Neuroimmunol. 2005; 169: 116-25.

Parkos, et al., CD47 mediates post-adhesive events required for neutrophil migration across polarized intestinal epithelia, J. Cell Biol., 1996 February; 132(3): 437-50

Penberthy T W, Jiang Y, Graves D T. Leucocyte adhesion molecules. Crit Rev Oral Biol Med 1997; 8(4):380-388.

Pignataro G, Meller R, Inoue K, Ordonez A N, Ashley M D, Xiong Z, Gala R, Simon R P. In vivo and in vitro characterization of a novel neuroprotective strategy for stroke: ischemic postconditioning. J Cereb Blood Flow Metab. 2008; 28(2):232-41. Epub 2007 Sep. 19. Erratum in: J Cereb Blood Flow Metab. 2008; 28(2):440. Gala, Rosaria [added].

Rowland R T, Meng X, Cleveland J C Jr, Meldrum D R, Harken A H, Brown J M. LPS-induced delayed myocardial adaptation enhances acute preconditioning to optimize postischemic cardiac function. Am J Physiol. 1997; 272:H2708-15.

Stevens S L, Ciesielski T M, Marsh B J, Yang T, Homen D S, Boule J L, Lessov N S, Simon R P, Stenzel-Poore M P. Toll-like receptor 9: a new target of ischemic preconditioning in the brain. J Cereb Blood Flow Metab. 2008; 28(5):1040-7.

Tager A M, and Luster A D. (2003). BLT1 and BLT2: the leukotriene B(4) receptors. Prostaglandins Leukot Essent Fatty Acids. 2003; 69: 123-134.

Tang S C, Arumugam T V, Xu X, Cheng A, Mughal M R, Jo D G, Lathia J D, Siler D A, Chigurupati S, Ouyang X, Magnus T, Camandola S, Mattson M P. Pivotal role for neuronal Toll-like receptors in ischemic brain injury and functional deficits. Proc Natl Acad Sci USA. 2007; 104: 13798-803.

Tasaki K, Ruetzler C A, Ohtsuki T, Martin D, Nawashiro H, Hallenbeck J M. Lipopolysaccharide pre-treatment induces resistance against subsequent focal cerebral ischemic damage in spontaneously hypertensive rats. Brain Res. 1997; 748:267-70.

Valen G. Cellular signalling mechanisms in adaptation to ischemia-induced myocardial damage. Ann Med. 2003; 35:300-7.

Valen G, Vaage J. Pre- and postconditioning in cardiac surgery. Bas Res Cardiol 2005; 100:179-86.

Vinten-Johansen J. Involvement of neutrophils in the pathogenesis of lethal myocardial reperfusion injury. Cardiovasc Res. 2004; 15; 61(3):481-97. Review.

Wang Z Q, Chen X C, Yang G Y, Zhou L F. U0126 prevents ERK pathway phosphorylation and interleukin-1 beta mRNA production after cerebral ischemia. Chin Med Sci J. 2004 December; 19(4):270-5.

Yellon D M, Hausenloy D J. Myocardial reperfusion injury. N Engl J Med. 2007; 13; 357(11):1121-35.

The invention claimed is:

1. A method for reducing recruitment, migration, or both recruitment and migration of polymorphonuclear cells to a site of inflammation associated with airway inflammation, wound healing, pleurisy, or reperfusion in an organ of a human patient, comprising administering locally to the organ or systemically to the patient in need thereof an isolated oligonucleotide having a phosphate backbone modification and selected from the group consisting of:
SEQ ID NO: 8 (IDX9059);
SEQ ID NO: 7 (IDX9054);
SEQ ID NO: 6 (IDX9045);
SEQ ID NO: 1 (IDX9005);
SEQ ID NO: 9 (IDX9074);
SEQ ID NO: 3 (IDX9022);
SEQ ID NO: 2 (IDX9010);
SEQ ID NO: 4 (IDX9030); and
SEQ ID NO: 13 (IDX0150),
in an amount effective to reduce recruitment, migration, or both recruitment and migration of polymorphonuclear cells to the site of inflammation and in a dose in the interval of about 1 to about 2000 µg/kg bodyweight of the patient.

2. The method according to claim 1, wherein the inflammation is associated with reperfusion of the organ and wherein the step of administering the isolated oligonucleotide is conducted before, simultaneous with, or after reperfusion of the organ.

3. The method according to claim 1, wherein the isolated oligonucleotide is administered in an amount sufficient to reduce surface expression of at least one receptor selected from the group consisting of chemokine (C—X—C motif) receptor 1 (CXCR1), chemokine (C—X—C motif) receptor 2 (CXCR2), and receptor leukotriene B4 receptor 1 (BLT1) on polymorphonuclear cells.

4. The method according to claim 1, wherein the reduced recruitment, migration, or both recruitment and migration of polymorphonuclear cells to a site of inflammation is a result of a down-regulation of at least one of the receptors chemokine (C—X—C motif) receptor 1 (CXCR1) and chemokine (C—X—C motif) receptor 2 (CXCR2).

5. The method according to claim 1, wherein the reduced recruitment, migration, or both recruitment and migration of polymorphonuclear cells to a site of inflammation is a result of a down-regulation of the receptor leukotriene B4 receptor 1 (BLT1).

6. The method according to claim 1, wherein the oligonucleotide is selected from the group consisting of:
SEQ ID NO. 8 (IDX9059); and
SEQ ID NO. 7 (IDX9054).

7. The method according to claim 1, wherein the administration is selected from the group consisting of: systemic, intraperitoneal, mucosal, oral, gastric, oesophagal, buccal, nasal, and pulmonary administrations.

8. The method according to claim 1, wherein the administration is selected from the group consisting of subcutaneous administration and intestinal administration.

9. A method according to claim 1, wherein the recruitment, migration, or both recruitment and migration of polymorphonuclear cells to a site of inflammation is associated with myocardial infarction, and wherein the oligonucleotide is administered before, after or simultaneously with the administration of a thrombolytic agent.

10. A method according to claim 1, wherein the recruitment, migration, or both recruitment and migration of polymorphonuclear cells to a site of inflammation is associated with stroke, and wherein the oligonucleotide is administered before, after or simultaneously with the administration of a thrombolytic agent.

11. A method for reducing ischemic damage and alleviating secondary reperfusion injury in a human patient having suffered or suspected of having suffered from a disturbance or interruption in the blood flow in an organ and scheduled for treatment, comprising administering locally to the organ or systemically to the patient before, simultaneously with, or after the scheduled treatment, an isolated oligonucleotide having a phosphate backbone modification and selected from the group consisting of:

SEQ ID NO: 8 (IDX9059);
SEQ ID NO: 7 (IDX9054);
SEQ ID NO: 6 (IDX9045);
SEQ ID NO: 1 (IDX9005);
SEQ ID NO: 9 (IDX9074);
SEQ ID NO: 3 (IDX9022);
SEQ ID NO: 2 (IDX9010);
SEQ ID NO: 4 (IDX9030); and
SEQ ID NO: 13 (IDX0150),
  in an amount effective to reduce ischemic damage and alleviate secondary reperfusion injury in the patient and in a dose in the interval of about 1 to about 2000 μg/kg bodyweight of the patient.

12. The method according to claim 11, wherein the oligonucleotide is administered in an amount sufficient to reduce surface expression of at least one receptor selected from the group consisting of chemokine (C—X—C motif) receptor 1 (CXCR1), chemokine (C—X—C motif) receptor 2 (CXCR2), and receptor leukotriene B4 receptor 1 (BLT1) on polymorphonuclear cells.

13. The method according to claim 11, wherein the organ is the heart and the oligonucleotide is administered in an amount sufficient to reduce recruitment, migration, or both recruitment and migration of polymorphonuclear cells to a site of inflammation in the organ.

14. The method according to claim 11, wherein the oligonucleotide is administered in an amount effective to prevent or alleviate secondary reperfusion injury following restoration of blood flow to the heart through the administration of a thrombolytic agent.

15. The method according to claim 11, wherein the oligonucleotide is administered in an amount effective to prevent or alleviate secondary reperfusion injury following restoration of blood flow to the heart through surgical intervention.

16. The method according to claim 11, wherein the oligonucleotide is administered in an amount effective to prevent or alleviate secondary reperfusion injury following restoration of blood flow to the heart through balloon angioplasty.

17. The method according to claim 11, wherein the oligonucleotide is administered in an amount effective to prevent or alleviate secondary reperfusion injury following restoration of blood flow to a transplanted organ in the patient.

18. The method according to claim 11, wherein the organ is the brain, and the ischemic damage is a secondary reperfusion injury.

19. The method according to claim 18, wherein the secondary reperfusion injury follows from restoring the blood flow to the brain through the administration of a thrombolytic agent.

20. The method according to claim 11, wherein the organ is liver, at least one kidney, intestines or part thereof, or at least one lung or part thereof, and the ischemic damage is a secondary reperfusion injury.

21. The method according to claim 11, wherein the secondary reperfusion injury follows from restoring the blood flow to the heart through by-pass surgery.

22. The method according to claim 11, wherein the administration is selected from the group consisting of: systemic, intraperitoneal, mucosal, oral, gastric, oesophagal, buccal, nasal, and pulmonary administrations.

23. The method according to claim 11, wherein the administration is selected from the group consisting of subcutaneous and intestinal administration.

24. The method according to claim 1, wherein the phosphate backbone modification is a phosphorothioate or phosphorodithioate modification.

25. The method according to claim 11, wherein the phosphate backbone modification is a phosphorothioate or phosphorodithioate modification.

* * * * *

UNITED STATES PATENT AND TRADEMARK OFFICE
CERTIFICATE OF CORRECTION

PATENT NO. : 10,046,006 B2
APPLICATION NO. : 14/512036
DATED : August 14, 2018
INVENTOR(S) : Charlotte Admyre et al.

Page 1 of 1

It is certified that error appears in the above-identified patent and that said Letters Patent is hereby corrected as shown below:

On the Title Page

Item "(30) Foreign Application Priority Data", change "0802338" to --0802338-4--.

Signed and Sealed this
Thirtieth Day of October, 2018

Andrei Iancu
*Director of the United States Patent and Trademark Office*

SEQUENCE LISTING

<160> NUMBER OF SEQ ID NOS: 16

<210> SEQ ID NO 1
<211> LENGTH: 25
<212> TYPE: DNA
<213> ORGANISM: Artificial Sequence
<220> FEATURE:
<223> OTHER INFORMATION: Synthesized

<400> SEQUENCE: 1
tcgtccatgg tcagggtccc ggggg                                              25

<210> SEQ ID NO 2
<211> LENGTH: 18
<212> TYPE: DNA
<213> ORGANISM: Artificial Sequence
<220> FEATURE:
<223> OTHER INFORMATION: Synthesized

<400> SEQUENCE: 2
tcccaagagt cgtccagg                                                      18

<210> SEQ ID NO 3
<211> LENGTH: 22
<212> TYPE: DNA
<213> ORGANISM: Artificial Sequence
<220> FEATURE:
<223> OTHER INFORMATION: Synthesized

<400> SEQUENCE: 3
tcgtcgttct gccatcgtcg tt                                                 22

<210> SEQ ID NO 4
<211> LENGTH: 21
<212> TYPE: DNA
<213> ORGANISM: Artificial Sequence
<220> FEATURE:
<223> OTHER INFORMATION: Synthesized

<400> SEQUENCE: 4
tcgtctgcca tggcggccgc c                                                  21

<210> SEQ ID NO 5
<211> LENGTH: 21
<212> TYPE: DNA
<213> ORGANISM: Artificial Sequence
<220> FEATURE:
<223> OTHER INFORMATION: Synthesized

<400> SEQUENCE: 5
tcgtcgattc gtctgccatg g                                                  21

<210> SEQ ID NO 6
<211> LENGTH: 13
<212> TYPE: DNA
<213> ORGANISM: Artificial Sequence
<220> FEATURE:
<223> OTHER INFORMATION: Synthesized

<400> SEQUENCE: 6
gggtcgcagc tgg                                                           13

<210> SEQ ID NO 7
<211> LENGTH: 15
<212> TYPE: DNA
<213> ORGANISM: Artificial Sequence

```
<220> FEATURE:
<223> OTHER INFORMATION: Synthesized

<400> SEQUENCE: 7
ggggtcgtct gcggg                                                   15

<210> SEQ ID NO 8
<211> LENGTH: 12
<212> TYPE: DNA
<213> ORGANISM: Artificial Sequence
<220> FEATURE:
<223> OTHER INFORMATION: Synthesized

<400> SEQUENCE: 8
gatcgtccgg gg                                                      12

<210> SEQ ID NO 9
<211> LENGTH: 19
<212> TYPE: DNA
<213> ORGANISM: Artificial Sequence
<220> FEATURE:
<223> OTHER INFORMATION: Synthesized

<400> SEQUENCE: 9
tcgttcgtct ttcgtctgc                                               19

<210> SEQ ID NO 10
<211> LENGTH: 23
<212> TYPE: DNA
<213> ORGANISM: Artificial Sequence
<220> FEATURE:
<223> OTHER INFORMATION: Synthesized

<400> SEQUENCE: 10
tttcgtctgc tttcgtttcg ttt                                          23

<210> SEQ ID NO 11
<211> LENGTH: 18
<212> TYPE: DNA
<213> ORGANISM: Artificial Sequence
<220> FEATURE:
<223> OTHER INFORMATION: Synthesized

<400> SEQUENCE: 11
tcgtctgctt tcgtctgc                                                18

<210> SEQ ID NO 12
<211> LENGTH: 16
<212> TYPE: DNA
<213> ORGANISM: Artificial Sequence
<220> FEATURE:
<223> OTHER INFORMATION: Synthesized

<400> SEQUENCE: 12
gatcgtccga tcgtcc                                                  16

<210> SEQ ID NO 13
<211> LENGTH: 19
<212> TYPE: DNA
<213> ORGANISM: Artificial Sequence
<220> FEATURE:
<223> OTHER INFORMATION: Synthesized

<400> SEQUENCE: 13
ggaacagttc gtccatggc                                               19
```

```
<210> SEQ ID NO 14
<211> LENGTH: 14
<212> TYPE: DNA
<213> ORGANISM: Artificial Sequence
<220> FEATURE:
<223> OTHER INFORMATION: Synthesized

<400> SEQUENCE: 14
ggggtcgtct gcgg                                                        14

<210> SEQ ID NO 15
<211> LENGTH: 22
<212> TYPE: DNA
<213> ORGANISM: Artificial Sequence
<220> FEATURE:
<223> OTHER INFORMATION: Synthesized

<400> SEQUENCE: 15
tgctgcttct gccatgctgc tt                                               22

<210> SEQ ID NO 16
<211> LENGTH: 12
<212> TYPE: DNA
<213> ORGANISM: Artificial Sequence
<220> FEATURE:
<223> OTHER INFORMATION: Synthesized

<400> SEQUENCE: 16
gatgctctgg gg                                                          12
```